(12) United States Patent
Mavroidis et al.

(10) Patent No.: US 6,379,393 B1
(45) Date of Patent: Apr. 30, 2002

(54) PROSTHETIC, ORTHOTIC, AND OTHER REHABILITATIVE ROBOTIC ASSISTIVE DEVICES ACTUATED BY SMART MATERIALS

(75) Inventors: Constantinos Mavroidis, Somerset; Charles Pfeiffer, Toms River; Kathryn J. DeLaurentis, Highland Park; Michael J. Mosley, Princeton, all of NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 0 days.

(21) Appl. No.: 09/395,623

(22) Filed: Sep. 14, 1999

Related U.S. Application Data
(60) Provisional application No. 60/100,127, filed on Sep. 14, 1998.

(51) Int. Cl.[7] ............................... A61F 2/70; A61F 2/66

(52) U.S. Cl. ........................................ 623/25; 623/57

(58) Field of Search ............................. 623/25, 24, 57, 623/58, 59, 60, 61, 63, 64, 66

(56) References Cited

U.S. PATENT DOCUMENTS

| | | | | |
|---|---|---|---|---|
| 3,866,246 A | * | 2/1975 | Seamore et al. | 623/25 |
| 4,246,661 A | * | 1/1981 | Pinson | 623/25 |
| 4,685,928 A | * | 8/1987 | Yaeger | 623/64 |
| 5,062,857 A | * | 11/1991 | Berringer et al. | 623/25 |
| 5,314,495 A | | 5/1994 | Kovacs | |
| 5,413,611 A | | 5/1995 | Haslam, II et al. | |
| 5,888,213 A | | 3/1999 | Sears et al. | |
| 6,090,139 A | * | 7/2000 | Lemelson | 623/2.1 |
| 6,109,852 A | * | 8/2000 | Shahinpoor et al. | 414/1 |

OTHER PUBLICATIONS

"A Clinical Experience with a Hierarchically Controlled Myoelectric Hand Prosthesis with Vibro-Tactile Feedback". Kyberd, P.J., Mustapha, N., Chappell, P.H., *Prosthetics and Orthotics International,* 1993, 17, 56–64.

"Shape Memory Alloy Actuated Robot Prostheses: Initial Experiments". Pfeiffer, C., DeLaurentis, K. and Mavroidis, C., *Proceedings of the 1999 IEEE International Conference of Robotics and Automation,* Detroit, MI, May 1999.

(List continued on next page.)

*Primary Examiner*—David H. Willse
*Assistant Examiner*—Alvin Stewart
(74) *Attorney, Agent, or Firm*—Hoffmann & Baron, LLP

(57) ABSTRACT

The present invention is directed to state-of-the-art medical devices using smart materials and related emerging technologies under development for robotics. In particular, the present invention is directed to the development of rehabilitative (i.e. prosthetic, orthotic, surgical) devices actuated by smart material artificial muscles to increase the dexterity and agility of an artificial limb or a dysfunctional body part, so that movement of the limb more accurately simulates movement of a human appendage. A kinetic assistive device is provided is provided which is constructed of a lightweight material (such as aluminum) and has a plurality of smart material actuators attached thereto. A system for detecting environmental stimulation of the device is provided in electrical communication with such actuators to effect movement of said device in response to detection signals produced thereby. The system includes a plurality of sensors, such as proximity detectors, accelerometers, tactile sensors and the like which are mounted on the assistive device and which provide data to computer-controlled command circuitry. This data can be encoded and used to control the movement of the assistive device via the actuators to more accurately predict the performance of the device in relation to that of an actual human limb.

66 Claims, 31 Drawing Sheets

OTHER PUBLICATIONS

"Shape Memory Alloy Actuated Robot Prostheses: Initial Prototypes". Pfeiffer, C., Mavroidis, C. DeLaurentis, K. and Mosley, M. *Proceedings of the 1999 ASME International Mechanical Engineering Congress and Exposition, Biomedical Engineering Division,* Nashville, TN, Nov. 1999.

"Design and Dynamics of a Shape Memory Alloy Wire Bundle Actuator". Mosley, M., Mavroidis, C. and Pfeiffer, C. *Proceedings of the American Nuclear Society, 8th Topical Meeting on Robotics and Remote Systems,* Pittsburgh, PA, Apr. 1999.

"Experimental Non–Linear Dynamics of a Shape Memory Alloy Wire Bundle Actuator", Mosley, M. and Mavroidis, C. *Proceedings of the 1999 ASME International Mechanical Engineering Congress and Exposition, Dynamics, Measurement and Control Division,* Nashville, TN, Nov. 1999.

"The SMART™ Wrist–Hand Orthosis (WHO) for Quadriplegic Patients". J.E. Makaran, D.K. Dittmer, R.O. Buchal and D.E. MacArthur. *Journal of Prosthetics and Orthotics,* 1992, vol. 5, No. 3, pp. 73–76.

Rehabilitation Medicine, Chapter 1, p. 1–2. H.A. Rusk, M.D. The C.V. Moxby Company, 1997, Fourth Edition.

"Myoelectric Prostheses", D.H. Silcox, III, M.D., M.D. Rooks, M.D., R.R. Vogel, M.D., and L.L. Fleming, M.D. *The Journal of Bone and Joint Surgery,* Inc., vol. 75–A, No. 12, Dec. 1993.

"Proportional Myoelectric Hand Control: An Evaluation", H.H. Sears and J. Shaperman. American Journal of Physical Medicine & Rehabilitation, 1991.

"The Artificial Substitution of Missing Hands With Myoelectrical Prostheses". M. Nader, Dr.–Ing. E.H., Sep., 1989.

"Feedback in Myoelectric Prostheses". R.N. Scott. Institute of Biomedical Engineering, University of New Brunswick, Canada. Sep. 1989.

"The Southampton Hand: An Intelligent Myoelectric Prosthesis", P.J. Kyberd, P.H. Chappell. *Journal of Rehabilitation Research and Development,* vol. 31, No. 4, Nov. 1994, pp. 326–334.

"Multifunctional Prosthetic–Robotics Systems. When?". A. Davalli, R. Sacchetti, H. Schmidl, INAIL Prosthesis Center, Budrio (Bologna, Italy).

"Myoelectric Teleoperation of a Complex Robotic Hand". K.A. Farry, I.D. Walker, R.G. Baraniuk. *IEEE Transactions on Robotics and Automation,* vol. 12, No. 5, Oct. 1996.

"A Single — DOF Multi–Function Prosthetic Hand Mechanism With An Automatically Variable Speed Transmission". G. Guo, X. Qian, W.A. Gruver, DE–vol. 45, Robotics, Spatial Mechanisms and Mechanical Systems, ASME 1992.

"On the Development of EMG Control for a Prosthesis Using a Robotic Hand". T. Iberall, G.S. Sukhatme, D. Beattie, G.A. Bekey. 1050–4729/94, 1994 IEEE.

"Mechanism Design of A New Multifingered Robot Hand", Li–Ren Lin and Han–Pang Huang. International Conference on Robotics and Automation. Minneapolis, Minnesota— Apr. 1996.

"Studies of Micro Actuators in Japan". B. Fujita, Institute of Industrial Science. University of Tokyo, Tokyo, Japan, 1989.

"A New Actuator of a Joint Mechanism Using TiNi Alloy Wire". K. Kuribayashi. *The International Journal of Robotics Research,* vol. 4, Winter 1986, © 1986 Massachusetts Institute of Technology.

"Millimeter Size Joint Actuator Using Shape Memory Alloy". K. Kuribayashi. IEEE , Salt Lake City, Utah, Feb. 20–22, 1989.

"Variable Structure Control of Shape Memory Alloy Actuators". D. Grant and V, Hayward. IEEE Control Systems, IEEE.

"Developmental of a Shape Memory Alloy Actuator. Improvement of Output Performance by the Introduction of a σ–mechanism". S. Hirose, K. Ikuta and K. Sato. *Advanced Robotics,* vol. 3, No. 2, pp. 89–108 (1989).

Prosthetic Usage in Major Upper Extremity Amputations. T.W. Wright, M.D., A.D. Hagen, M.D., M.B. Wood, M.D. *Journal of Hand Surgery,* 20(4): 619–622, 1995.

"State of the Art in Upper–limb Prosthetics". Lamb, D.W. *Journal of Hand Therapy,* 6(1): 1–8, 1993.

Caldwell, D.G. and Taylor, P.M., "Artificial Muscles as Robotic Actuators" IFAC Robot Control Conference (Syroc 88) Karlsrue, Germany, pp. 401–406, 1988.

\* cited by examiner

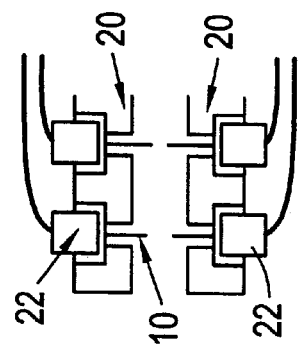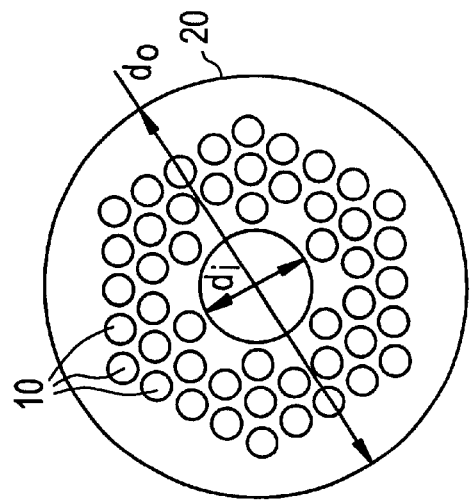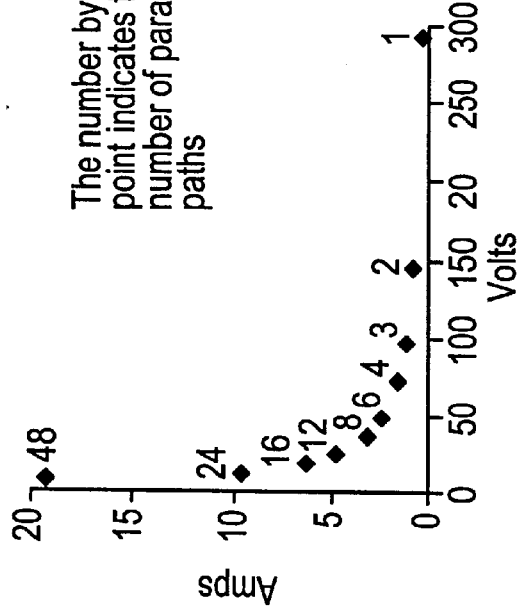

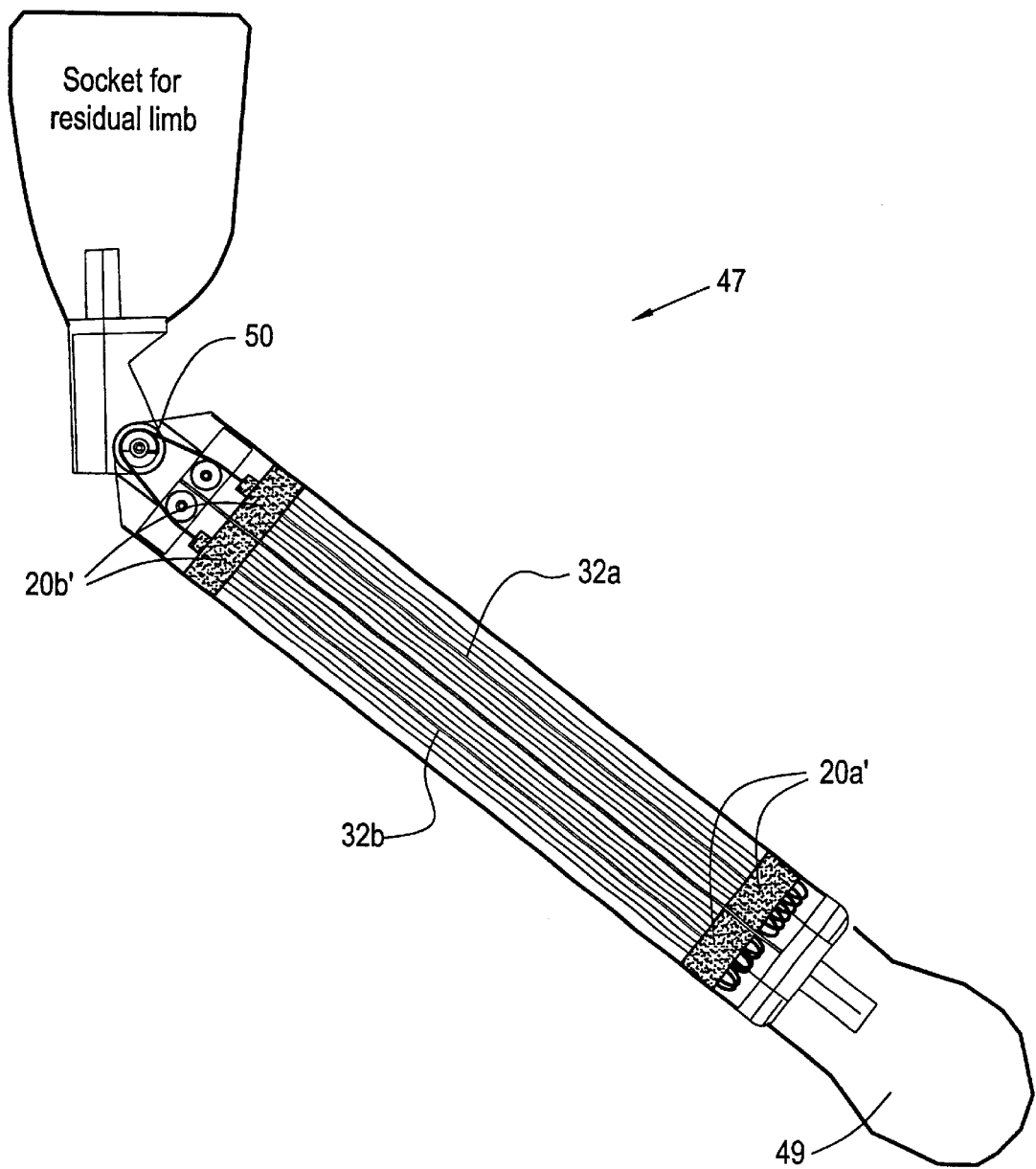

Example "A"  Example "B"

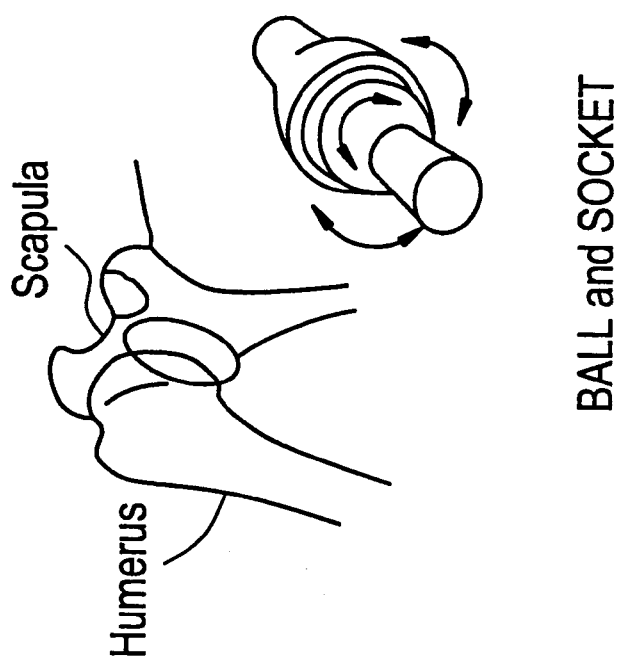

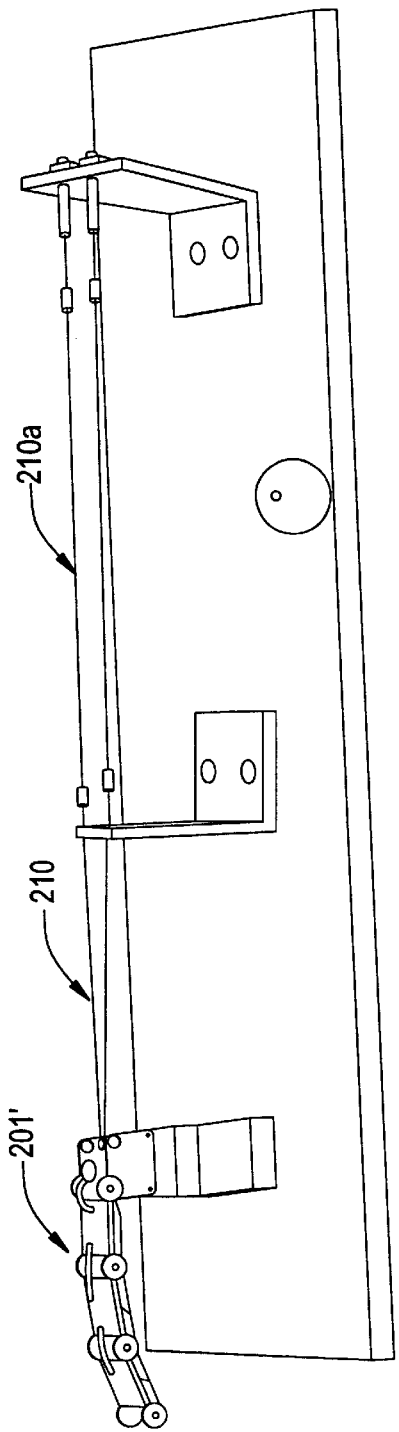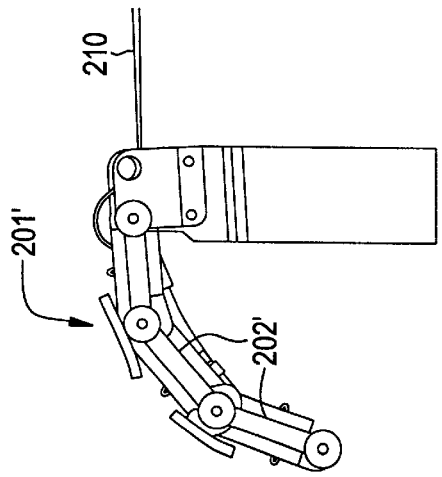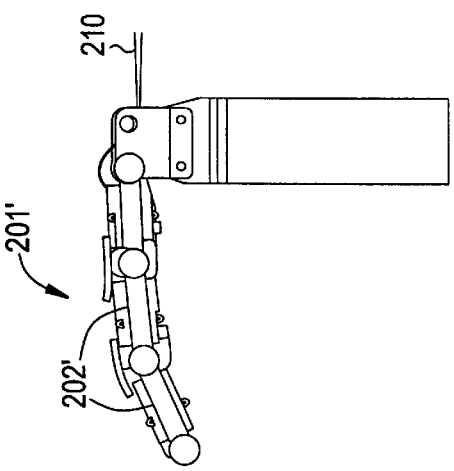

PROSTHETIC, ORTHOTIC, AND OTHER REHABILITATIVE ROBOTIC ASSISTIVE DEVICES ACTUATED BY SMART MATERIALS

This application claims the benefit of U.S. Provisional Application No. 60/100,127, filed Sep. 14, 1998 and entitled "Robot Prostheses Actuated by Shape Memory Alloys".

FIELD OF THE INVENTION

The present invention relates to an assistive device, such as a prosthetic, orthotic, surgical or other rehabilitative device, which improves the freedom of movement capabilities of artificial limbs or dysfunctional body parts. More specifically, this invention is directed to an assistive device which is actuated by smart materials and which includes force and torque sensors to more accurately replicate the freedom of motion and sensory capabilities of human limbs.

BACKGROUND OF THE INVENTION

For the more than 43 million Americans with disabilities, and millions of other such patients worldwide, rehabilitation with orthotic and prosthetic (O&P) care subsequent to amputation or injury is a healthcare solution which addresses the problems of escalating healthcare costs and limited access to quality care. Studies have shown that for every dollar spent on rehabilitation, many more dollars are saved by enabling disabled patients to resume normal daily activities after an injury has occurred. When the costs of long-term care are compared to the savings realized by patient rehabilitation, long term care can include institutionalization, adult day care and custodial care at home. Rehabilitation generates revenue because rehabilitated people are more likely to return to work and resume paying taxes, thereby ending claims of wage compensation. Rehabilitation patients are also less likely to require consistent, long-term medical attention. Rehabilitative care and research is, therefore, essential if people with injuries and disabilities are to achieve and maintain independence. (Source: "About Orthotics and Prosthetics", www.adbiomech.com/oandpcare.html, 1999.)

Recently, the possibility of merging robotic and rehabilitative technologies has been expressed with great interest in rehabilitative applications. During the last fifteen years, multi-degree of freedom robot arms and dexterous robotic hands have been built to perform autonomously fine and delicate tasks. Based on this technology, researchers have started experimenting on the electromyographic (EMG) control of multi-fingered hands, tele-operation of complex robotic prosthetic hands, implementation of force sensory feedback on myoelectrically controlled forearm prostheses and design of multi-function robot prosthetic hand mechanisms.

Current actively controlled prostheses, however, have only one or two controlled degrees-of-freedom that are actuated by low power motors. Most extremity prostheses currently in use have a terminal device (such as a hand or hook) controlled either by movements of a shoulder girdle transmitted via a cable (i.e. body powered), or by myoelectric control (i.e., motors triggered by the contraction of muscles in the residual limb). In the latter control method, electrodes embedded in the socket of a prosthesis detect EMG signals generated by contraction of the residual muscles of an amputated limb. These signals provide a trigger for battery powered DC motors which move a hand, elbow and/or wrist of the prosthesis.

Such prostheses, however, provide limited ability to grasp and manipulate small objects. Control of the force of the grip is very gross, due to the lack of sensory feedback. In addition, the weight of the motors, their associated support structures and accompanying gearing systems increase the weight of the prosthesis. Furthermore, excessive system noise obviates the important aesthetic qualities of an assistive device. Improved control of multiple degrees of freedom, along with the provision of sensory feedback, would greatly refine the function of such prostheses.

Robotic systems have also been proposed to perform important tasks in non-medical applications where anthropometrical movement is preferred but human intervention presents inherent risks. Examples of such activities include removal of hazardous waste and decommissioning of nuclear sites. Since these tasks occur in a highly radioactive environment, robotic and other automated systems are required to reduce worker exposure to radiation. Robots operating in these remote and hazardous conditions must have a high weight lifting capability and be able to cover a large workspace. At the same time, they must be lightweight for easy transportation and dexterous enough to move in a cluttered environment. However, existing robotic systems for macro manipulation are characterized by poor payload to weight ratio and are often cumbersome and voluminous.

The conventional systems used to meet the above described robotic applications demonstrate a plethora of limitations. Weak, heavy and voluminous actuators are often incompatible with human anatomy. In addition, a lack of advanced sensory interfaces and the use of conventional control approaches impede interaction between human and artificial members. Human upper and lower limbs have tactile sensing, can perceive changes in temperature and sense when a force is exerted upon the limb as well as judge the appropriate application of a force. Current prosthetic and manipulative articulated devices do not offer these capabilities.

In an effort to reproduce the agility and sensory capabilities of human limbs, current research has sought to mechanically reproduce joint systems on a macro-mechanical scale analogous to the actual dimensions of human limbs. Such research not only includes the testing of mechanical joints themselves, but also the use of contracting materials, such as muscle wire, to imitate muscle motion as it occurs in the human anatomy. Previous macro-mechanical systems which have been created use complex and heavy linkage-type mechanisms that are mostly actuated by electrical motors (i.e., stepper motors, dc servo motors, etc.). These systems are highly dependent upon the unique range of capabilities of the particular device being tested and constructed. Such systems require extensive investments of time and resources that directly increase costs not only due to testing delays but also due to increased difficulty in manufacturing the resulting robotic device.

The present invention addresses the need for a new type of assistive device that is lightweight and provides a better sensory interface among the user, the device and the stimuli in the surrounding environment. Significant weight reduction is realized in a device that uses smart materials as artificial muscle actuators of system joints. The overall interface is improved by incorporating advanced sensors into the design, such as force/torque sensors which sense the weight of the artificial limb and monitor the interactive forces between the wearer and the surrounding environment. There are numerous applications for such devices in physical medicine as a replacement or support for joints, such as legs, hands, feet, knees and elbows. Additionally, these concepts can be used in other robotic systems such as joysticks, haptic interfaces and any other articulated mechanical systems.

SUMMARY OF THE INVENTION

It is an object of the present invention to provide an assistive device that more accurately simulates the mobile and sensory capabilities of human limbs.

It is further an object of this invention to provide an assistive device which is actuated by smart materials.

It is still further an object of this invention to provide an assistive device which implements sensors to more accurately detect interaction between the wearer and the environment.

It is still further an object of the present invention to improve the lifting capabilities of assistive devices.

It is still further an object of the present invention to improve the mobile and sensory capabilities of assistive devices.

In the efficient attainment of these and other objectives, the present invention is directed to state-of-the-art medical devices using smart materials and related emerging technologies under development for robotics. In particular, the present invention is directed to a kinetic assistive device actuated by artificial muscles for providing increased dexterity and agility of an artificial limb. The assistive device is constructed of a lightweight material such as aluminum having a plurality of smart material actuators anchored thereto. A system for detection environmental stimulation on the device is provided in electrical communication with such actuators to effect movement of said device in response to detection signals produced thereby. The system includes a plurality of sensors, such as proximity detectors, accelerometers, tactile sensors and the like which are mounted on the assistive device and which provide data to computer-controlled command circuitry. This data can be encoded and used to control the movement of the assistive device via the actuators to more accurately predict the performance of the device in relation to that of an actual human limb. In this manner, artificial limbs can be constructed that are lightweight, compact and dexterous so as to mimic human anatomy and maintain a high lifting capability.

BRIEF DESCRIPTION OF DRAWINGS

FIG. 2 shows a plot of current and voltage requirements for actuation of a smart material wire bundle of the present invention based on different electrical current paths through the bundle.

FIG. 3 shows an illustrative arrangement of smart material artificial muscle actuator wires on a bundle end plate.

FIG. 4 shows an illustrative crimping schematic for smart material actuator wires fastened between a pair of bundle end plates.

FIG. 8 shows a schematic of an illustrative smart material actuator configuration of the present invention utilized in a prosthetic elbow.

FIG. 14A shows a perspective view of a human shoulder joint and a ball and socket simulating actual motion of such shoulder joint.

FIG. 33 shows an articulated finger prototype.

FIG. 34 shows the articulated finger prototype of FIG. 34 before and after actuation thereof.

DESCRIPTION OF THE PREFERRED EMBODIMENTS

The present invention is based on the use of smart material artificial muscles to power the joints of prosthetic, orthotic, rehabilitative and other robotic devices that mimic the. Smart materials are materials that change some aspect of their dimension and exert forces due to temperature, voltage or pressure change. For example, for smart material artificial muscles fabricated out of Ni—Ti A ("Nitinol") shape memory alloy ("SMA"), a change in length is effected by a temperature and stress dependent phenomenon called the "shape memory effect" wherein temperature changes cause the material to shift phases back and forth between martensite and austenite. The simplest way to heat a Nitinol wire and initiate the phase change is by sending a current through the material, thereby creating an increase in temperature due to resistive heating.

The advantages of smart materials include, but are not limited to, their incredibly small size, volume and weight, their high force to weight ratio, their novel reactive force properties, their low cost and their antiropometrical behavior. The group of smart materials anticipated for use with the present invention includes electrostrictive polymers, electrostatic devices, piezoelectric, polymers, mechanochemical polymer/gels, shape memory polymers and shape memory alloys. The materials considered for use with the present invention are hereinafter referred to collectively as "smart materials" or "SM" and are not limited to the materials enumerated above, but also include materials later developed that are conducive to the operation and objectives of the present invention.

Muscle Fiber Bundle Construction

The emphasis of the present invention is the construction, placement and control of assistive robotic devices which utilize a plurality of SM actuators to translate contraction and/or expansion of the actuators into predictable movement of the device. Typically, a single smart material element can only apply a limited force which is insufficient for practical rehabilitative applications such as those described hereinabove. With the present invention, several pluralities of smart material wires can be "bundled" to form a strong artificial muscle with superior lifting capability. As with biological muscle fibers, the artificial muscle actuators of the present invention can be further divided into different sets, each of which is independently controlled by application of appropriate voltage levels. The artificial muscles thereby have the ability to generate forces with high resolution. In this disclosure, the terms "artificial muscles", "artificial muscle actuators", "smart material actuators" and "SM wire bundles" will be used synonymously to refer to the artificial muscles that actuate the devices anticipated herein.

Figure 1:
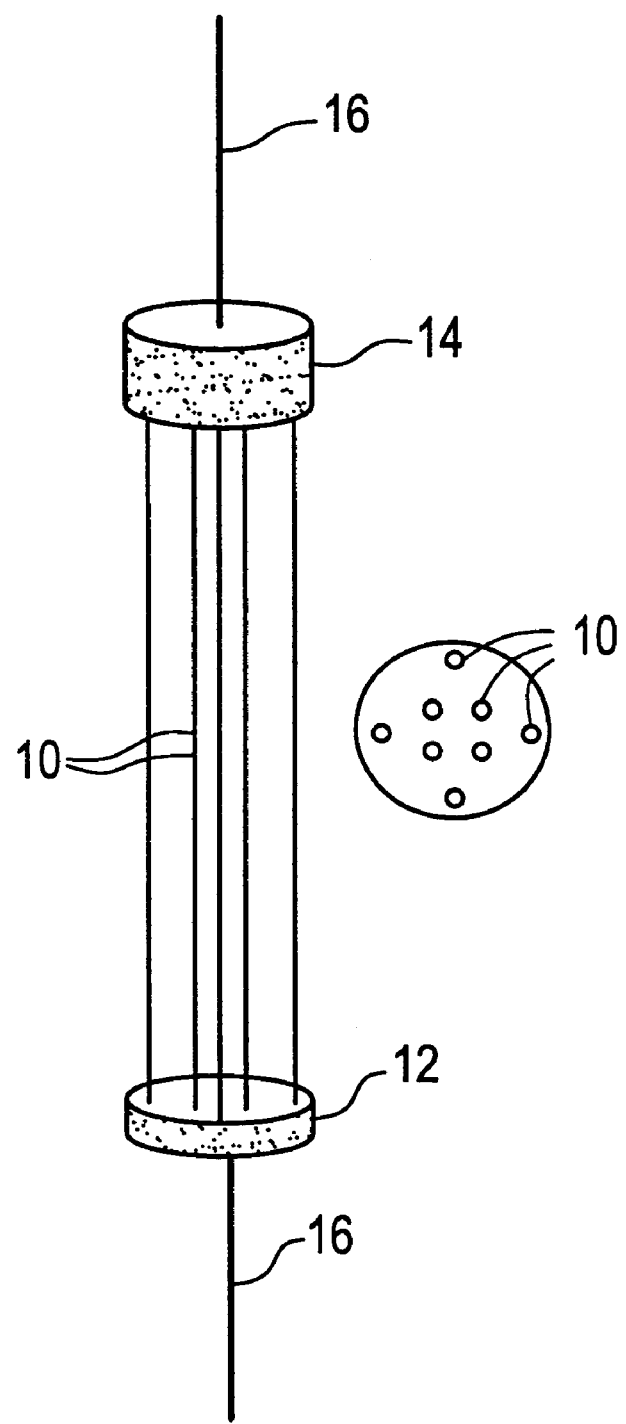
FIG. 1 shows a schematic view of a smart material wire bundle of the present invention.

Now referring to the figures and with particular reference to FIG. 1, the concept of applying large forces using SM wire bundles is achieved by strategically arranging a bundle of smart material wires 10 between a lower end plate or muscle bracket 12 and an upper end plate Ad or muscle bracket 14. Bracket 14 includes a plurality of diodes and resistors embedded therein which measure environmental stimulation (i.e. force, displacement, etc.) on the artificial muscle arrangement. As with an actual muscle configuration, each of brackets 12 and 14 is connected to a tendon 16 that connects the artificial muscle to a support structure (not shown) actuated thereby. A detailed description of the placement of muscle wires on a support member will be described further hereinbelow.

When attaching SM wire bundles to a support member for actuation thereby, consideration must be given to the parameters of the wire used. SM bundle design has four key parameters that determine the load capability, displacement capability and current/voltage requirements for effecting proper actuation of an assistive device by an SM artificial muscle actuator. These parameters are the diameter of the wire, the number of wires, the length of the bundle and the number of parallel current paths. It is preferable to bundle many wires mechanically in spaced parallel relation to one another, thereby increasing the force capability of the actuator. For Nitinol and similar materials, the bandwidth of a wire is largely determined by heat transfer through the surface of the wire, and changing the surface to volume ratio of the SM actuator drastically changes the actuator's performance. It is therefore better to use several thin wires instead of only a few thick wires to improve the force capabilities of a Nitinol or similar SM actuator without sacrificing bandwidth.

Referring back to FIG. 1, wires 10 preferably remain in spaced parallel relation, and thus out of contact with one another, so that a cooling medium (i.e. air) can evenly dissipate heat from all wire surfaces. Hence, the best way to increase the force capability without sacrificing actuation time is to connect many thin wires mechanically in parallel with space between the wires.

For the electrical arrangement of the wires, using different numbers of parallel paths allows the bundle to be tailored to different applications where there may be current or voltage restrictions. The preferred circuit design for the bundle itself is one that avoids a combination of low voltage and very high amperage. A circuit is created where the wires are arranged electrically in a combination of series and parallel paths while remaining mechanically connected in parallel. For a combination of SMA wires in series and parallel electrical connections, for example, it is provided:

$$V_B = I_{SMA} * \frac{N}{P} * L * \overline{R}$$

and $$I_B = P * I_{SMA}$$

where $V_B$ and $I_B$ respectively represent the voltage drop across and current through an SMA wire bundle; $I_{SMA}$ represents the actuation current in a single wire; N represents the number of wires in the bundle; P represents the number of parallel paths; L represents the bundle length; and R represents the linear resistance of a single wire.

By way of example, for the case where there are 48, 0.006" (150 μm) wires, FIG. 2 shows a plot of current and voltage requirements in order to achieve actuation current (400 mA) in each wire for different numbers of parallel paths. It is noted that the ratio N/P must be equal to an integer if identical paths are constructed.

In the case of Nitinol and similar smart material wires, using thicker wires or connecting many wires mechanically in parallel will increase the force capabilities of a smart material actuator. However, the actuator bandwidth and power supply requirements may be dramatically affected by such an arrangement and should be considered when designing an SM bundle actuator. One of the parameters that greatly affects the bandwidth of a Nitinol wire actuator, for example, is the wire diameter. Even though a 0.006" (150 μm) diameter wire may lift 0.728 lbs (330 g) and require 2 seconds before it is ready to cycle again, a 0.012". (300 μm) diameter wire may lift 2.76 lbs (1250 g) and require 8 seconds before it is ready to cycle again. The reason for this behavior is the change in surface to volume ratio of the wires and, thus, the resultant change in heat transfer characteristics.

EXAMPLE

An Ni—Ti SM bundle actuator is constructed to apply an arbitrarily large force. The actuator applies a maximum force of 100 lbf (445 N) over a distance of approximately 0.5 in. (1.27 cm). Given that Ni—TI wires can contract 5 to 8% of their original dimension, a bundle length of 12 in. (30.5 cm) was selected to meet the displacement criterion.

Simple experiments conducted to determine the weight lifting capability of different diameter Ni—Ti wires reveal that a single 0.006" (150 μm) wire can lift over 2 lbs. (0.9 kg) and possess a sufficiently rapid cycling time for application in an artificial muscle bundle. Considering that one wire can lift over 2 lbs., in theory, fifty 0.006" wires connected mechanically in parallel can lift at least 100 lbs. In the end, 48 wires were used due to the symmetry of arrangement into a cylindrical bundle. Additionally, the number 48 is evenly divisible by 10 integers which makes it convenient for varying the number of parallel paths.

Referring now to FIG. 3, a Ni—Ti SM bundle was constructed consisting of 48, 12" (30.5 cm) long, 0.006" (150 μm) diameter wires (N=48, L=12 in). The 48 wires were connected mechanically in parallel between two circular Teflon end plates 20, each having an inner diameter $d_i$ and an outer diameter $d_o$ as shown . Teflon was selected due to its high dielectric strength, temperature resistance and good mechanical stability. Since all wires are not at the same voltage due to their electrical arrangement, it was necessary to keep each one electrically isolated from the others at the end plates.

Each wire was passed through end plates 20 and was terminated with a copper crimp to provide superior mechanical and electrical connection as shown in FIG. 4. The copper crimps fit tightly into 48 corresponding sockets machined into each end plate, producing 96 total crimps. The 48 wires were arranged in a hexagonal close packed array, resulting in a compact bundle (see FIG. 3). Each of the copper crimps was then connected to a short section of electrical wire and thereafter connected to four (two for each side) 25-pin parallel connectors for easy connection and removal from a power circuit.

Figure 5:
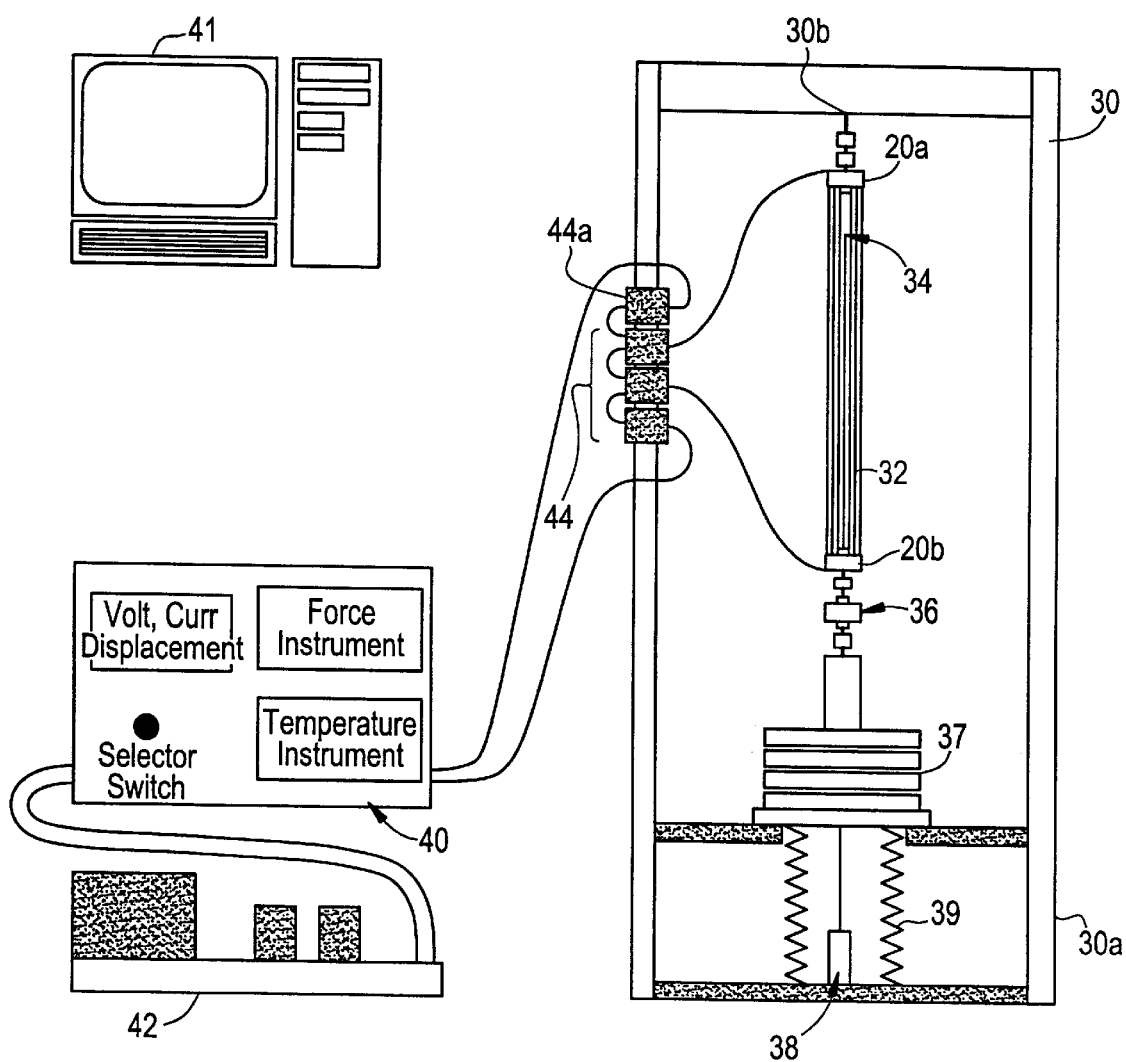
FIG. 5 shows a testing apparatus used to determine the performance characteristics of a smart material actuator of the present invention.
Figure 6A:
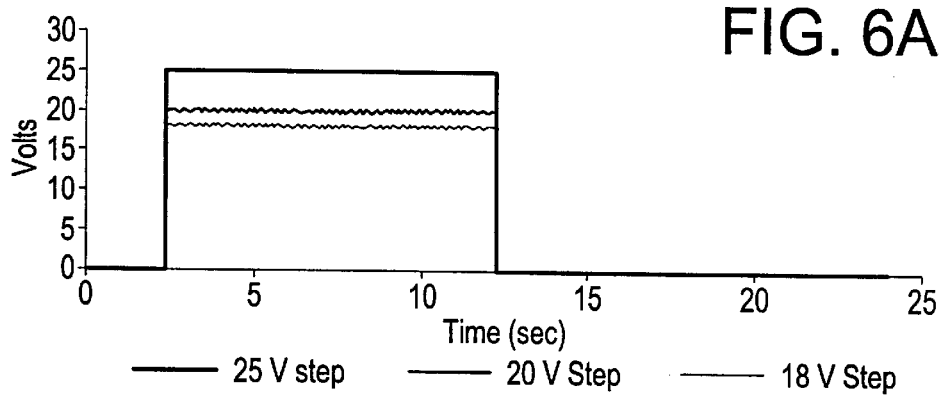
FIG. 6 shows data obtained from the test apparatus presented in FIG. 5 for a smart material actuator of the present invention.
Figure 6B:
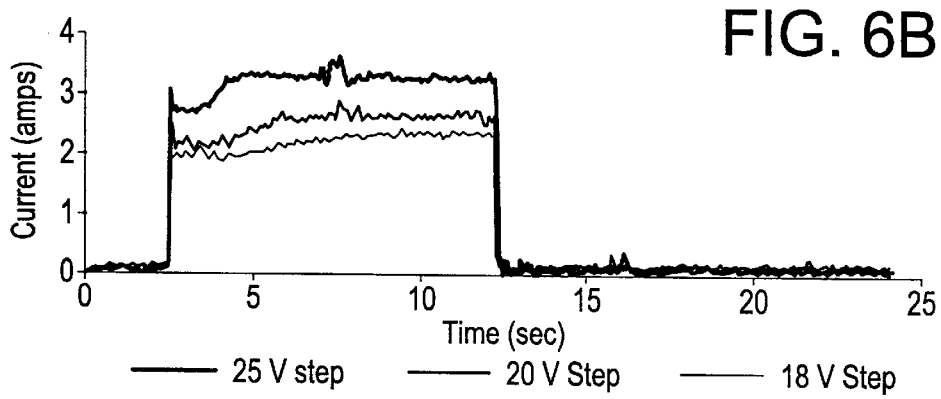
Figure 6C:
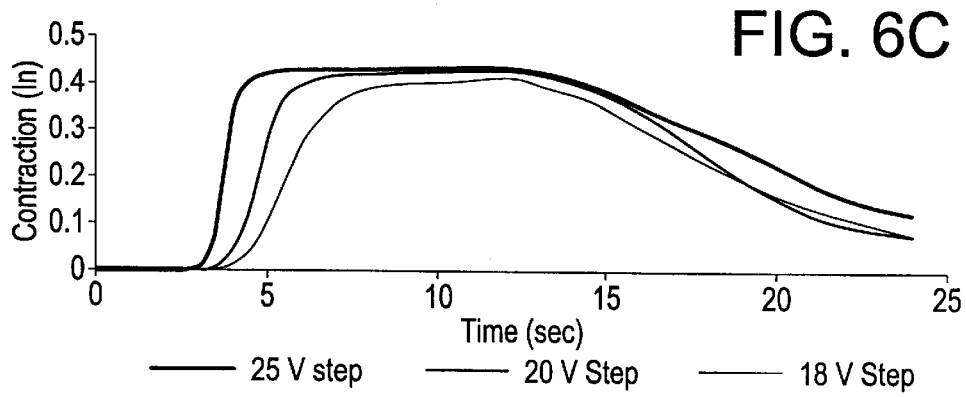
Figure 6D:
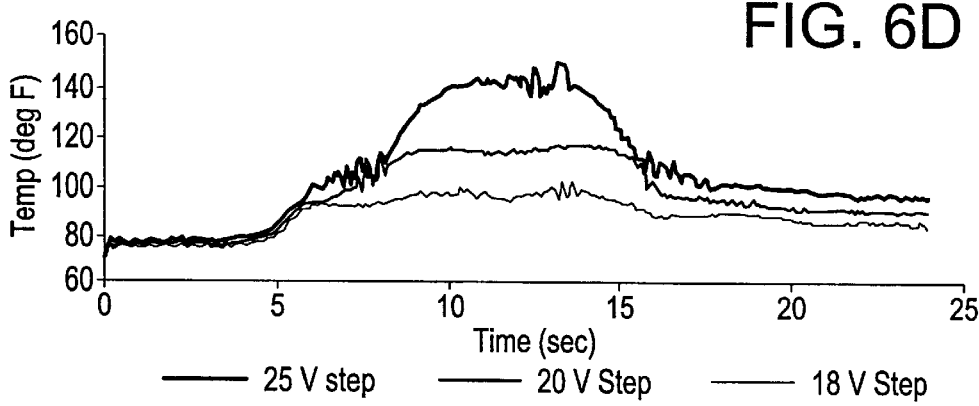

In order to determine the performance characteristics of the Ni—Ti SM bundle actuator, an experimental setup was designed and constructed as shown in FIG. 5. The experimental setup includes test rig 30, power supply 42, control and instrumentation unit 40 and a PC 41. Test rig 30 includes a frame 30a, SM bundle 32, load cell 36 and corresponding electrical power connections.

Frame 30a provides a rigid hanging point 30b for an upper end of SM bundle 32. An opposed lower or "free" end of the vertically oriented bundle is connected to a load cell 36. A variable weight 37 and/or a spring 39 may also be provided to act as the SM bundle load. Test rig 30 is particularly designed for convenient installation, adjustment and removal of all components and sensors mounted to an experimental support structure.

For this experimental setup, in order to vary the number of parallel electrical paths a through SM bundle 32, a "patch terminal" system 44 is provided. Terminal system 44 includes a plurality of patch terminals 44a. It is noted that terminal system 44 is provided only for testing purposes and is not intended for use in an assistive device such as a prosthesis. Patch terminals 44a as used herein include four 48-pin cannon plugs. One of the four plugs is wired such that there is a one-to-one correspondence between each pin in the plug and the end of each Ni—Ti SM wire at a top end plate 20a. A second plug is similarly wired for a bottom end plate 20b.

As discussed hereinabove, changing the number of parallel paths changes the voltage and current requirements of the bundle. For a large number of parallel paths, a low voltage and high current is needed. For a small number of parallel paths, a high voltage and low current is needed. Therefore, a third plug is wired such that all pins were at a HI (+) supply voltage. The fourth plug was similarly wired for a LO (−) return voltage. A set of short patch wires was used to create the desired current path through the bundle.

The control and instrumentation unit 40 contains the necessary circuitry to control the raw voltage from the power supply. Additionally, it includes the sensors, meters, and wiring needed to measure and display force, bundle displacement, current, voltage, and air temperature within the bundle. This unit also provides the required connection ports to receive input signals from, and send data to, PC 41. The raw voltage from the power supply was controlled using a custom designed operational amplifier circuit.

SMA bundle 32 was tested through open loop experiments using the setup described above. Patch terminals 44a were wired for 8 parallel paths with 6 wires in series for each parallel path. Referring back to FIG. 2, this results in a theoretical actuation voltage of 36.6 V and a current of 3.2 A for complete contraction of bundle 32.

For the open loop experiments described herein, a variable weight 37 was provided in place of load cell 36. The specific weights used were 11 lbs. (4.99 kg) and 27.5 lbs. (12.5 kg). Several different types of input signals (step, ramp, sinusoid, and half sinusoid) were defined and then sent to the SM Bundle. Each experimental run lasted approximately 24 seconds during which the following data was recorded: bundle voltage drop, bundle current, bundle contraction and air temperature at the center of the bundle.

A complete set of data for three different step input signals with an 11 lb. load is shown in FIG. 6. Looking at the bundle contraction plot, a dry friction phenomenon is observed as contraction initiates. It takes a finite amount of time for the Ni—Ti wire to reach actuation temperature, resulting in a delay. Additionally, it takes time for the tension in bundle 32 to rise to the weight of the load, at which point the load starts to lift. Larger step voltages cause faster heating and thus a shorter delay before the system responds.

Furthermore, an almost linear, first order system rise to a maximum deflection is realized. The slope of the linear response changes with the magnitude of the step. Larger magnitudes result in faster responses. A reasonably stable steady state deflection is reached and a saturation phenomenon is observed for large voltages. It is also clear that when operating near maximum deflection, a large increase in the step voltage (and the corresponding current) results in only a very small increase in bundle contraction.

Referring again to FIG. 6, and specifically to the bundle contraction curves when voltages of 18 V and 25 V are applied (generating a current of 2.2 and 3.2 amps, respectively), a comparison of such curves shows a difference in deflection of only 0.03". To improve efficiency, therefore, bundle 32 should be operated in a region somewhat below the maximum contraction when used in an assistive device.

Figure 7A:
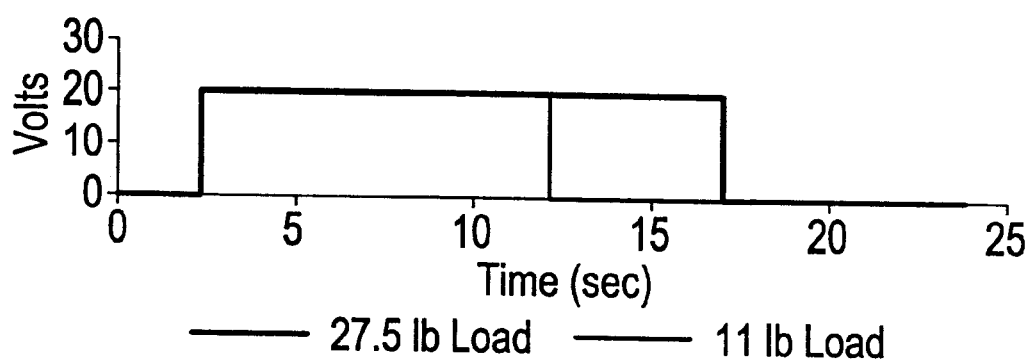
FIG. 7 shows a response comparison for different loads obtained from the test apparatus of FIG. 5 for a smart material actuator of the present invention.
Figure 7B:
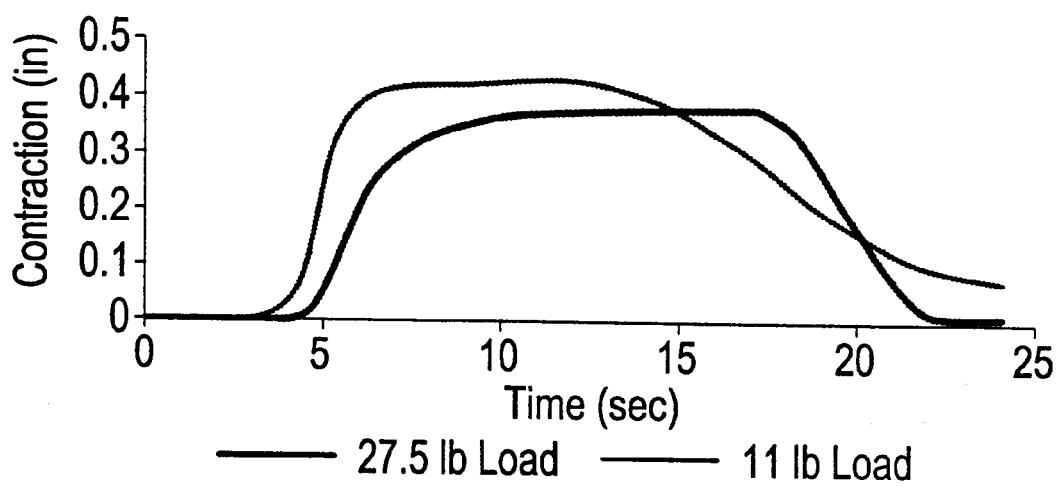

Similar step input signals were applied to SM bundle 32 with a 27.5 lb. load. The resulting plots, shown in FIG. 7, had similar characteristics to those where the load was 11 lbs. FIG. 7 particularly shows the contraction of bundle 32 due to a 20 V step input with the two different loading conditions (11 lb. and 27.5 lb.). Voltage was applied and maintained for a shorter period of time for the 11 lb. load to capture the decay of the bundle contraction when the input voltage dropped to 0. As expected, the contraction is greater and more rapid for the lighter load. Furthermore, the contraction decay following removal of the input signal is slower for the lighter load.

For the same 20 volt step input signal, contraction begins earlier when the load is 11 lbs. than when the load is 27.5 lbs. This can be explained by considering the two opposing strains that exist in an SM wire that is contracting under a load. There is a negative strain due to the shape memory effect and there is a positive strain due to elasticity. Examining the dynamics of the experimental setup, the free end of the SM bundle starts to move when the tension in the bundle is equivalent to the weight of the load. Until this equilibrium point is reached, the elastic strain cancels the strain due to the shape memory effect. Therefore, for the larger load, more shape memory strain is needed to cancel the elastic strain. As a result, there is a longer delay before the load starts to move.

Elastic strain also explains the difference between the maximum steady contraction for an 11 lb. load and a 27.5 lb. load. At the maximum contraction, the difference in elastic strains can be calculated in the following manner:

$$\Delta L = \frac{PL}{AE}$$

where P is the load (11 or 27.5 lb.), L is the length of the bundle (12 in. (30.5 cm)), A is the combined cross sectional area of all 48 wires ($1.36e^{-3}$ in$^2$ ($8.77e^{-3}$ cm$^2$)), and E is Young's Modulus for Ni—Ti (approximately $6.96e^6$ psi (48 GPa)). Therefore, the theoretical difference between the two elastic strains is:

$$(\Delta L)_{27.5} - (\Delta L)_{11} = (27.5 - 11 \text{ lb})\left(\frac{L}{AE}\right) \approx 0.02 \text{ in.}$$

The same calculation in metric units yields approximately 0.05 cm.

The process described above and the applicable theory are easily put into practice with an assistive device such as elbow prosthesis 47 shown in FIG. 8. The actuation of a smart material wire bundle in an assistive device can be achieved in a manner similar to that described above. In elbow prosthesis 47 a hand prosthesis 49 is fixed to bundle end plates 20a' having flexion SM bundle 32a and extension SM bundle 32b attached thereto. Bundles 32a and 32b are likewise attached at opposed ends to free end plates 20b' which are in mechanical communication with a pulley 50.

The arrangement shown in FIG. 8 provides a support structure similar to a humerus section of a human arm such that bundles 32a and 32b enable prostheses 47 and 49 to extend, flex, rotate or move otherwise via associate flexion and extension of the SM wire actuators. This configuration, though representative of the manner of operation of the SM actuators of the present invention, is merely illustrative of the applications anticipated by the present invention.

Achieving Large Motions with Small Actuator Displacements

With 5 to 8% deflection available, the Nitinol artificial muscle actuator of the above examples illustrates the precision with which SM actuators should be attached to an assistive device support member in order to achieve large motions. For a simple mechanism consisting of a moving link that pivots about a fixed revolute joint, small linear displacements of any SM actuator can be converted into large angular motions by (1) fixing one end of the actuator and (2) attaching a free end of the actuator to the moving link close to the center of rotation of the revolute joint. Such a configuration replicates the manner in which biological muscles move skeletal components or "links".

Figure 9:
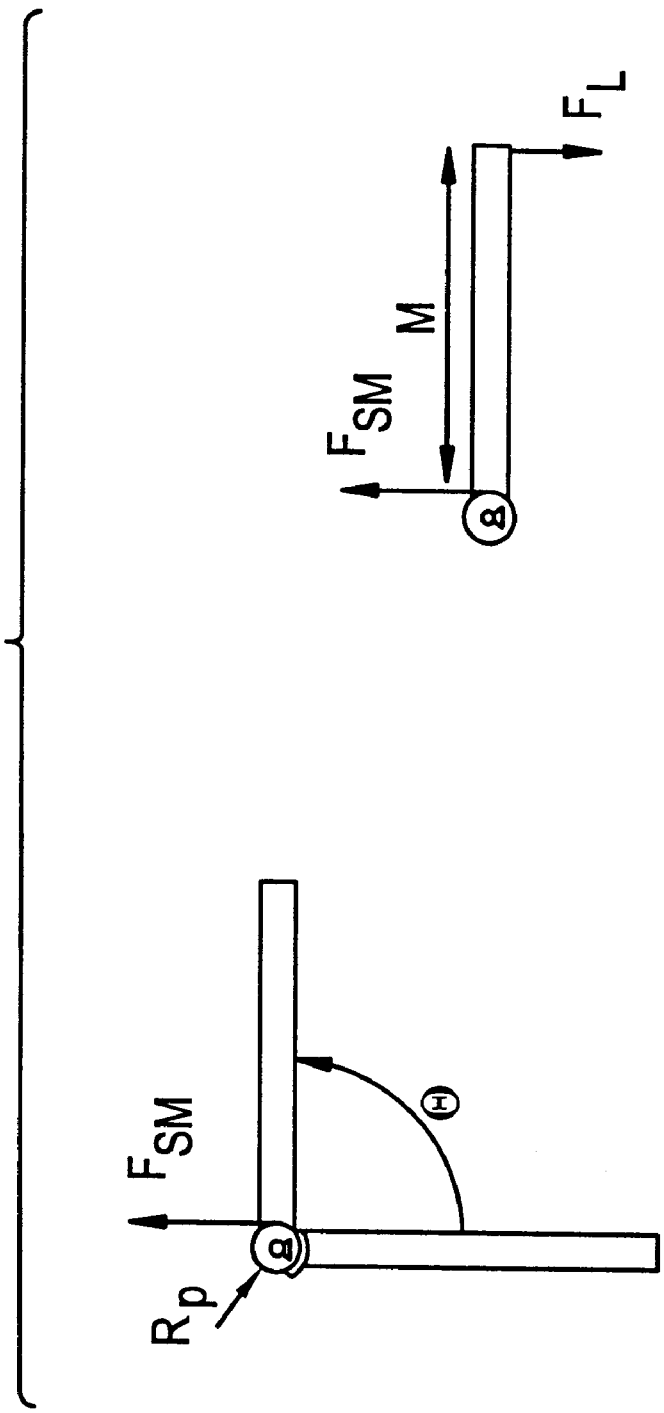
FIG. 9 shows a schematic of a large angular deflection for a smart material actuator of the present invention.

FIG. 9 shows a schematic of one way to achieve large angular deflections from an SM artificial muscle actuator for use in an assistive device. If the SM actuator pulls on a small, flexible cable that wraps around and fastens to a pulley fixed to a moving link, the relationship between the required pulley radius, $R_p$, the maximum SM deflection, $\Delta_{SM}$, and the desired angular deflection θ of the moving link, is:

$$R_p = \frac{\Delta_{SMA}}{\Theta}$$

For large angular deflections, $R_p$ must typically be small compared to the length M of the moving link. Considering a static problem, the resulting ratio of the required actuation force, $F_{SM}$, to the load, $F_L$ is:

$$\frac{F_{SMA}}{F_L} = \frac{\Theta M}{\Delta_{SMA}}$$

From the above two equations, it is clearly seen that if SM actuators are used in macro-robotic systems with revolute joints, the large angular motion requirement is satisfied by attaching the SM artificial muscle actuator closer to the revolute joint axis.

Figure 10:
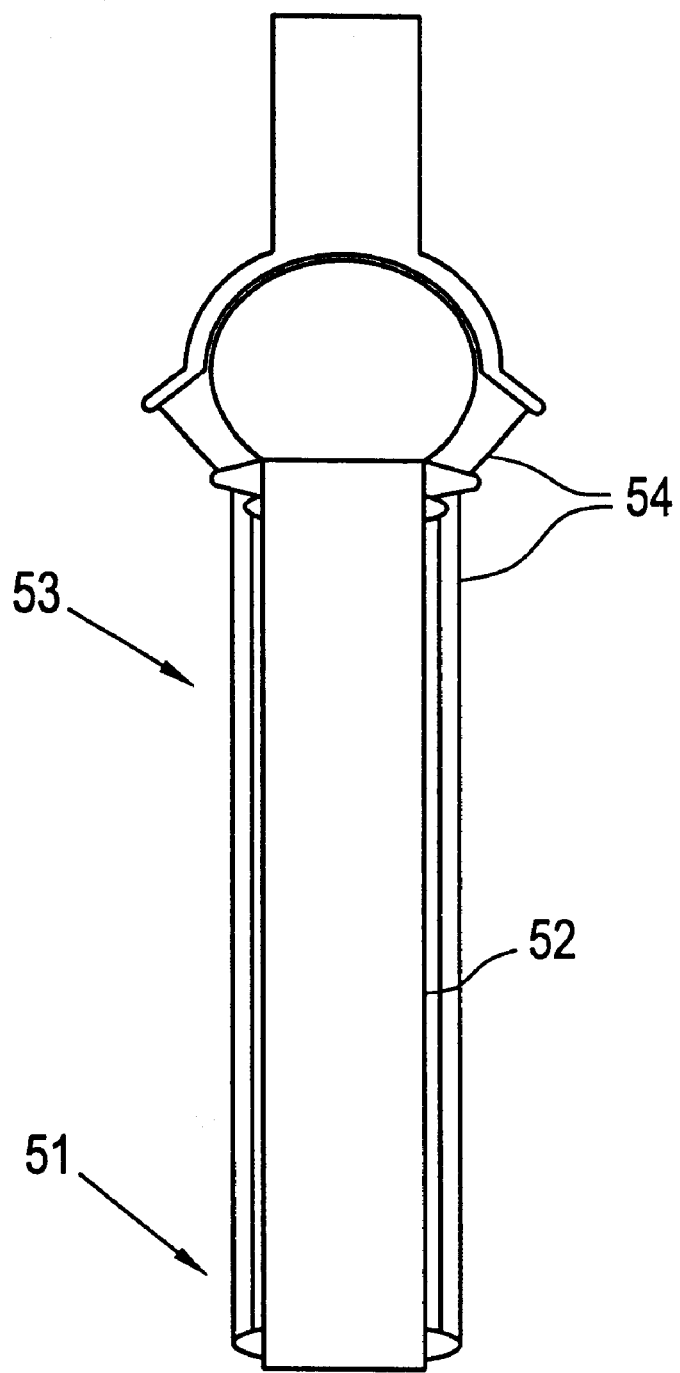
FIG. 10 shows a smart material actuator of the present invention in a folded overlapping configuration along a length of a support member.

As illustrated in FIG. 10, specific techniques can be employed and adapted to ensure that smart material artificial muscle actuators perform well when used in assistive devices. When large limb motions are desired, very long smart material wires are preferred, since some smart materials contract or expand only a small percentage of their original length. In most cases, the required wire length will be much larger than the length of a structural member where the wire is attached. To overcome this problem, a plurality of anchor pivots can be provided around a support member to enable overlapping of the smart material wires along a length of the member. A In FIG. 10, at least one anchor pivot 51 is provided at a free extremity of support member 52 for support of at least one smart material element 53 thereby. Element 53 can be placed at each end of a structural member such as spherical joint 54 so as to be folded in an overlapping manner along the length of member 52. In this manner, the effective length of element 53 can be multiplied to amplify the range of motion.

Figure 11:
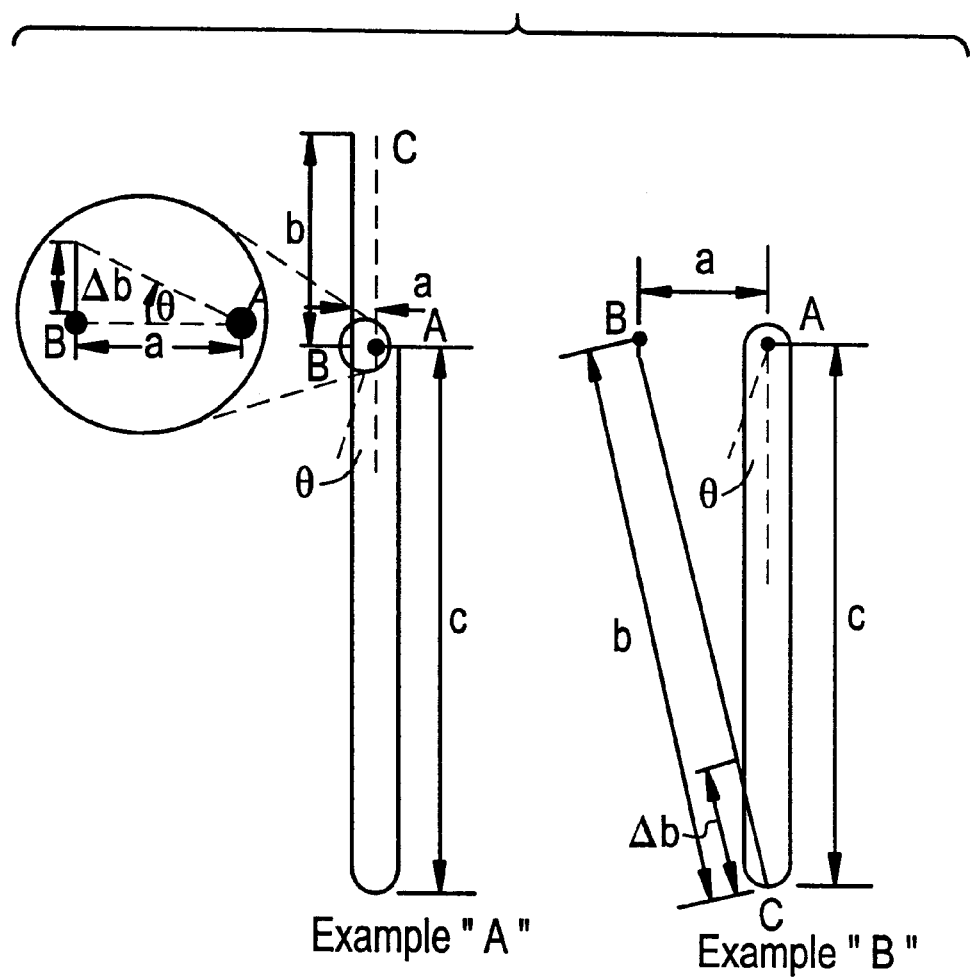
FIG. 11 shows a schematic of two methods for attaching a smart material actuator to a structural support member.

A challenge in using smart material artificial muscles to actuate prosthetic limbs, therefore, is to create a large angular motion from a small amount of linear displacement from the smart material wires. Consider a rod of length 'c' that can rotate using a revolute joint A around an axis as shown in FIG. 11. The actuation of the joint is done with smart material wire BC of length 'b' that can exhibit a maximum displacement $\Delta b$.

Two methods of attaching wire BC on rod C are considered, both of which are inspired by the attachment of human muscles that are responsible for muscle movement. In one method, point B is attached on rod C, very close to the center of joint A, and point C is attached at a fixed point away of the center of joint A (see Example A in FIG. 11). In Example A, the maximum angle $\theta$ of rotation of rod C is the ratio of the wire contraction $\Delta b$ to the distance 'a':

$$\theta = \frac{\Delta b}{a} \quad (1)$$

The smaller the distance 'a' is, the larger the angle $\theta$ becomes.

In an alternative method, point C is attached on rod C at a location close to the free end of the rod (i.e. opposite joint A), and point B is placed at a fixed location close to joint A (see Example B in FIG. 11). In Example B, the sine law in triangle ABC at the contracted configuration results in the formula:

$$\sin(90 - \theta) = \cos(\theta) = \frac{(\alpha + \Delta\alpha)(b - \Delta b)}{a} \quad (2)$$

where $\alpha + \Delta\alpha$ is the angle BCA in the extreme (i.e. contracted) configuration of the SM wire and the angle $\alpha$ is the angle BCA in the zero (i.e. vertical) configuration. The sine law in the triangle ABC at the zero angle configuration (vertical position of the rod) is therefore written as:

$$1 = \frac{ab}{a} \quad (3)$$

Both angles $\alpha$ and $\alpha + \Delta\alpha$ are considered small, and a small angle approximation is used to determine $\sin(\alpha$ and $\alpha+)$ and $\sin(\alpha)$. If Equation (2) is subtracted from (3) and only first order terms are considered, then:

$$2\sin^2(\theta/2) = 1 - \cos(\theta) = \frac{\alpha \Delta b - b \Delta \alpha}{a} \quad (4)$$

Equation (4) verifies the conclusion that angle $\theta$ is large when distance 'a' is small. Both examples thereby show that large motions are achieved by affixing SM artificial muscle wires a very small distance 'a' from one of the rod ends.

Figure 11A:
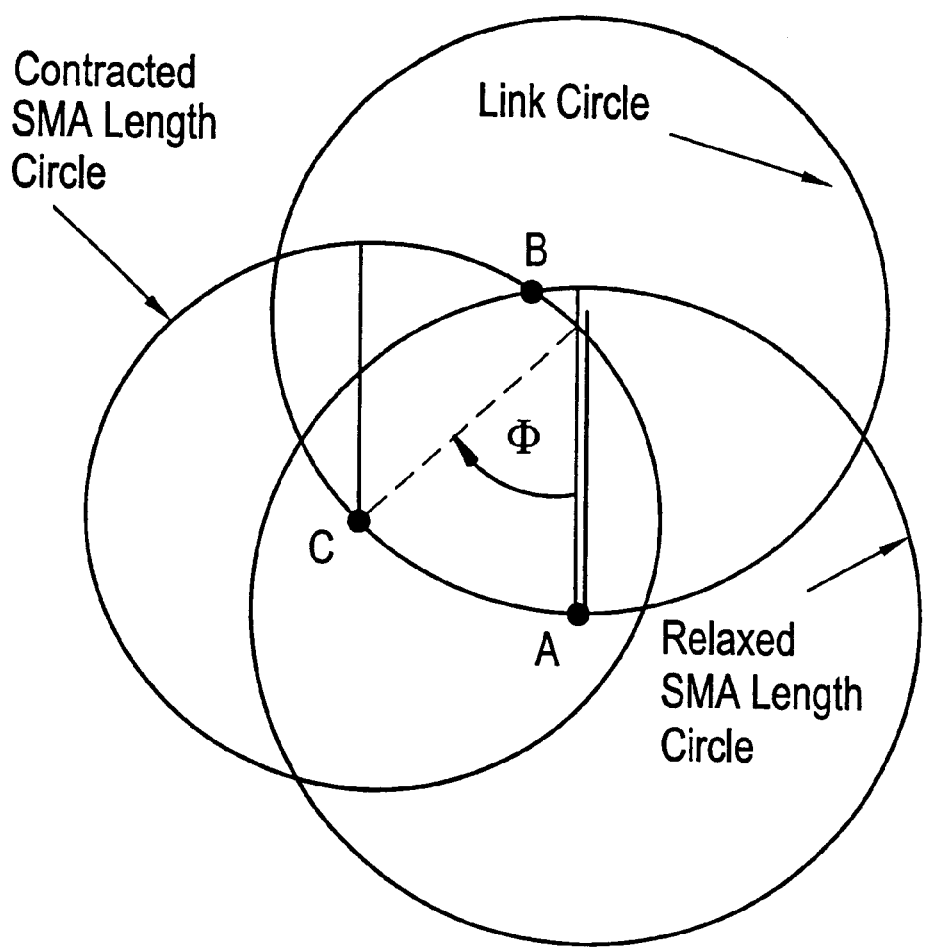
FIG. 11A shows a schematic of a method of the present invention for determining the placement for attachment of smart material actuators on a structural support member.

To generate large angular motions, it becomes important to determine the fixed attachment point for placement of the SM wire on a support member. The attachment point on a moving member, especially in anthropometrical artificial limbs, can be determined by the graphical method shown in FIG. 11A. Considering again Example B from FIG. 11, one end of the SM muscle wire BC is attached at point C, the free end of the rod, and the other end of the SM muscle wire is attached at a fixed point B outside the rod. It is desired to determine the location of point B when it is known that the rod has a length 'c', the SM wire at the zero configuration has a length 'b', the maximum contraction of the wire is $\Delta b$ and the maximum desired angle of rotation is $\Phi$. Point B is located at the intersection of the two circles. One circle is drawn having as its center point A at the zero configuration and radius b (see "Relaxed SMA Length Circle" in FIG. 11A). The other circle is drawn having as its center point C at the extreme configuration with radius b-$\Delta b$ (see "Contracted SMA Length Circle" in FIG. 11A). The two intersecting points of these circles give two solutions to this problem corresponding to the upper or lower configuration of the rod. A similar method can be developed for Example A in FIG. 11.

Installation of a Feedback System in SM Artificial Muscle Actuated Prostheses Robotic devices developed in accordance with this invention are also equipped with a feedback system in signal communication with SM artificial muscle actuators. Such a system includes a plurality of sensors such as force/torque sensors and a vibro-tactile based haptic interface to transfer force, torque, acceleration and other information to the patient. The patient will thereby control the interaction forces between the assistive device and the patient's environment.

As an illustration, an exemplary force feedback system may consist of a six-axis force/torque sensor that will be placed at the wrist of an arm-hand prosthesis and miniature force/tactile sensors at the fingertips. The wrist force-torque sensor will measure the forces and moments applied at an artificial hand either by the weight of objects that are carried by the prosthesis or by the environment (i.e. pushing or pulling forces) when an amputee performs a task. These forces, on a much smaller scale, will be transferred to the patient with a tactile system that is placed on the body of the patient. Every time the person lifts an object, (s)he will then feel a small force proportional to the weight that is lifted. The fingertip force-tactile sensors will provide information for the grip force. All force/torque information will be taken into account by the person during the EMG control of the artificial limb.

Figure 12:
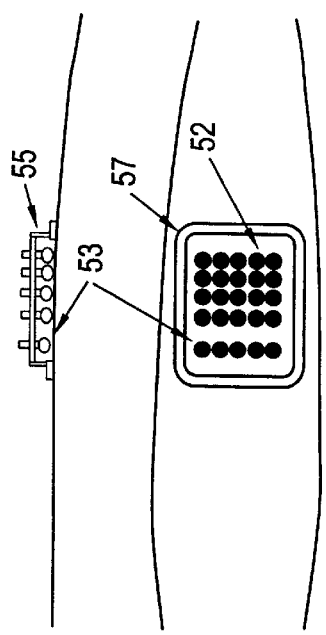
FIG. 12 shows a schematic of a matrix array of microsolenoids for a vibro-tactile system used in conjunction with a robotic device of the present invention.

A conventional vibro-tactile system may also be provided which consists of a matrix sensory array 52 of micro-solenoids 53 as shown in FIG. 12. The micro-solenoids press against the skin when energized. Each micro-solenoid has the capability of operating at different amplitudes and frequencies. Solenoids 53 are held in place by a lightweight plastic frame 55 which has a light adhesive border 57 surrounding the bottom of the array. Adhesive border 57 serves as the physical connection between sensory array 52 and the patient.

EMG Control of Smart Material Actuated Devices

Advanced robot control techniques are used in the control of the novel assistive devices of the present invention. The command inputs for these controllers can be generated using EMG signals obtained from the patient's residual muscles. As sensors gather information from the patient's environment, EMG signals are gathered from the patient. Both types of signals are used to assist with control of the device.

Sensors will be added to devices depending upon the function of the sensor and the design and purpose of the assistive device. For instance, tactile sensors such as those described above may be placed on or near the surface of a device of the present invention, whereas a force sensor may be placed on the surface or inside of the device. It is the function of the sensors to inform the device when too much pressure has been applied or when the device is too close to an object. Detection is accomplished via a signal sent from the sensor to a computer within command circuitry that controls the function of the device according to predetermined criteria for pressure or force. For example, for an arm prosthesis, a maximum force supportable by the prosthesis is determined for lifting capabilities, so that when such force is exceeded, the command circuitry prohibits the device to function.

Multi-channel EMG control of an SM-actuated assistive device can also be utilized. An example of such an EMG control is a below-elbow design having three degrees-of-freedom: wrist flexion/extension, thumb flexion/extension and flexion/extension of digits two and three moving together. The three degrees-of-freedom are controlled by six EMG channels (two directions for each degree of freedom). EMG signals will be detected from six muscles of the forearm from bipolar surface electrode pairs embedded in a prosthesis socket. Wrist flexion/extension will be controlled by the SM artificial muscle equivalents of the pronator teres and supinator muscles, respectively. Flexion and extension of digits two and three will be controlled by the equivalent SM flexor digitorum superficial and extensor digitorum muscles, respectively. Flexion of the thumb will be controlled by the brachioradialis muscle, and extension of the thumb will be controlled by the extensor carpi radialis muscle. Contraction of the extensor muscles will open the digits, allowing the hand to open sufficiently to grasp an object. Relaxation of the extensor muscles will allow the hand to close passively into the rest position, closing around the object, and contraction of the flexor muscles will increase the grip force proportional to the level of contraction.

Feedback from sensors in an assistive device allow the user to detect environmental stimulation on an assistive device, such as the strength of the grip of a prosthetic hand, the force required to lift an object with a prosthetic arm and the speed with which an orthotic head brace rotates in response to neck rotation. The patient can thereby adjust the assistive device according to the needs of the task. The EMG signals will be amplified using a differential amplifier to produce a signal with minimal noise and a rapid rise time. The resulting voltage will trigger shortening of the SM artificial muscles proportional to the amplitude of the EMG signal.

Figure 13:
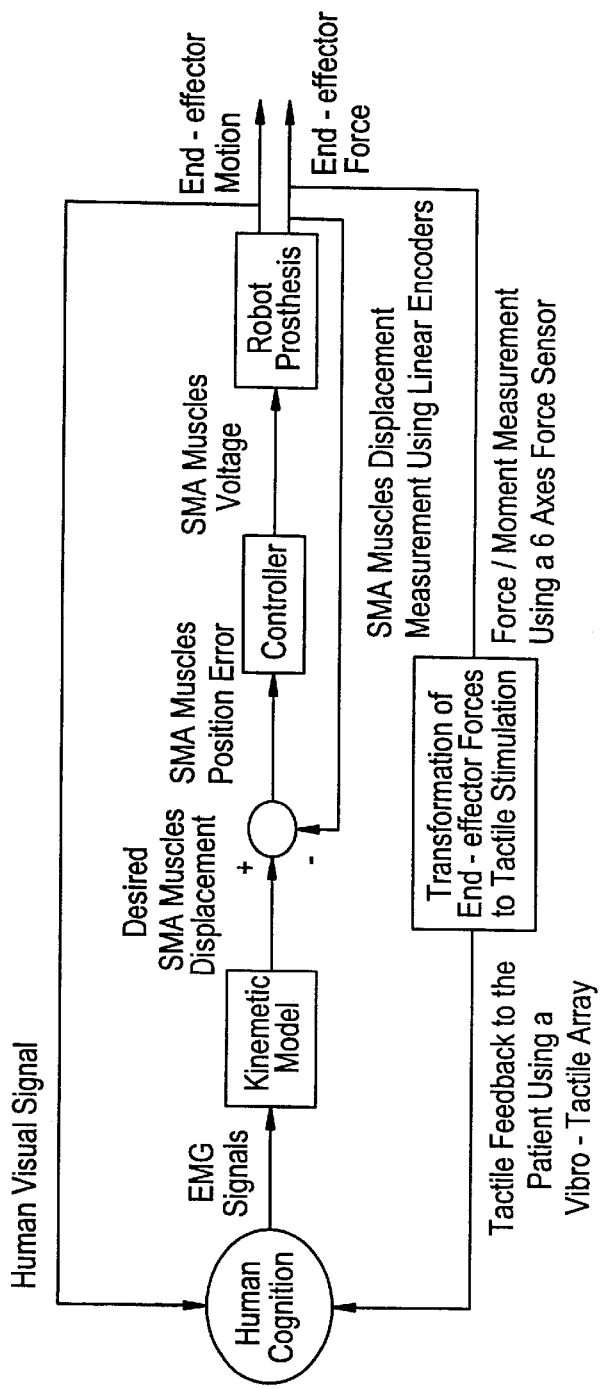
FIG. 13 shows a block diagram of robot prosthesis position and/or force control used in controlling smart material actuated prostheses of the present invention.
Figure 14:
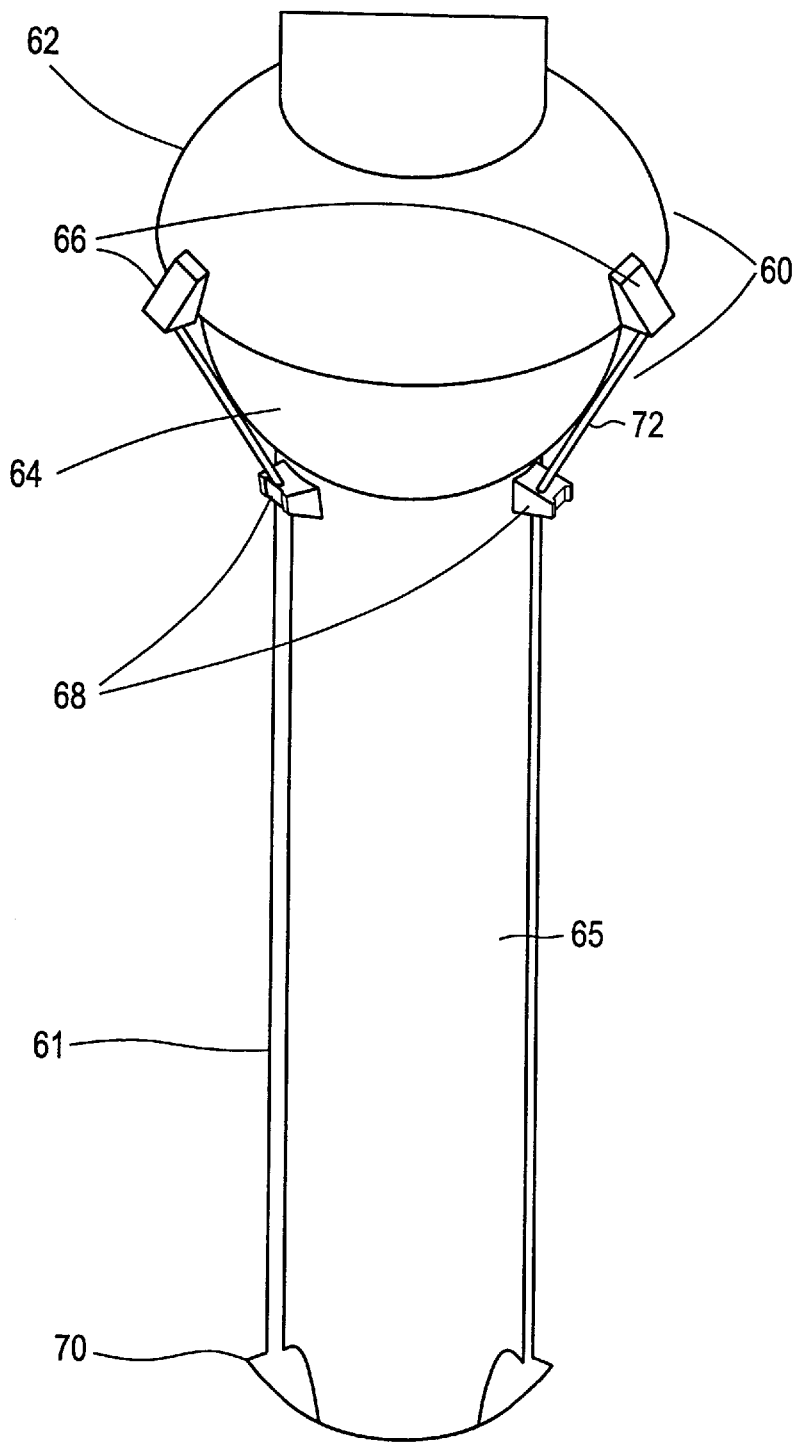
FIG. 14 shows a perspective view of a spherical shoulder joint of the present invention.

A block diagram of a robot prostheses position and/or force control consistent with the above described operation is shown in FIG. 13. This diagram model is consistent with robotic control systems used currently in rehabilitative devices to control the movement thereof, however, other similar EMG control methods can be utilized for various assistive devices constructed in accordance with this invention.

Design of Assistive Devices Having Smart Material Artificial Muscle Actuators Design of prototypical devices in accordance with the present invention can now be described. Three examples of prosthetic limb devices are shown in this section, including a shoulder, an elbow and a multi-fingered hand with a dexterous wrist. However, it is understood that this discussion is by way of example only and does not limit the scope of this invention to the specific uses shown herein. The goal of these examples is to show that SM actuators can be used in large mechanical systems, apply large forces, generate large motions, and can be used as actuators in systems emulating human parts.

Shoulder Prototype

Spherical joints in mechanical systems are very difficult to actuate. When spherical motion is needed in a joint of a mechanical system, it is often accomplished by linkages composed of one degree of freedom revolute joints, which are actuated by DC motors. The consequence of this solution is the need to design heavy, voluminous and complex systems to produce spherical joint motion. A common example would be the spherical wrist employed in some industrial manipulators.

In humans, there are many joints that have a motion similar to a spherical joint. The shoulder and the hip provide two examples. In this disclosure, an assistive device in the form of a spherical joint is presented that was built to emulate the human shoulder joint. It is actuated with SM linear actuators using an antagonistic scheme similar to that of biological systems.

Referring now to FIGS. 14–17, a novel two-degree-of-freedom ball and socket spherical joint system 60 actuated by smart material muscle wires 61 is shown. Joint system 60 exhibits motion very similar to the motion of a human shoulder, illustrated in FIG. 14A. Joint system 60 includes as primary components a plurality of smart material ("SM") artificial muscles 61 which emulate shoulder muscle movement; a support member or shaft 65 which emulates the humerus and provides a muscle attachment surface; a ball portion 64 which emulates the ball portion of the joint; and socket portion; and a socket portion or cup 62. Each of cup 62, ball portion 64 and shaft 65 is preferably machined of a lightweight material such as aluminum, however, other materials such as such as cast metal may be used which are conducive to the operation and maintenance of the assistive device as disclosed herein.

Ball portion 64, which is the moving part of joint system 60, provides a spherical machined surface defined at an upper extremity of shaft 65, a hollow, lightweight and generally cylindrical member. Ball portion 64 fits within cup 62 with a tolerance that permits smooth movement therebetween with minimum friction. A spacer insert (not shown) may also be provided which snaps into cup 62 to further ensure smooth operation of ball portion 64 and cup 62.

In order to replicate two degree-of-freedom movement, a minimum of three SM wires 61 is required with the wires equidistantly positioned (i.e. 120° relative to one another) around the circumferential surface of shaft 65. Wires 61 are attached to shaft 65 proximate ball portion 64. Wires 61 act in an antagonistic manner such that when at least one wire is pulling in one direction, other wires will pull in an opposite direction. This arrangement emulates anatomical muscle actuation in biological systems, ensuring stable and smooth movement of the joint. Although the illustrated design has two rotational degrees-of-freedom, designs having three degrees-of-freedom can also be realized, as discussed hereinbelow.

Figure 15:
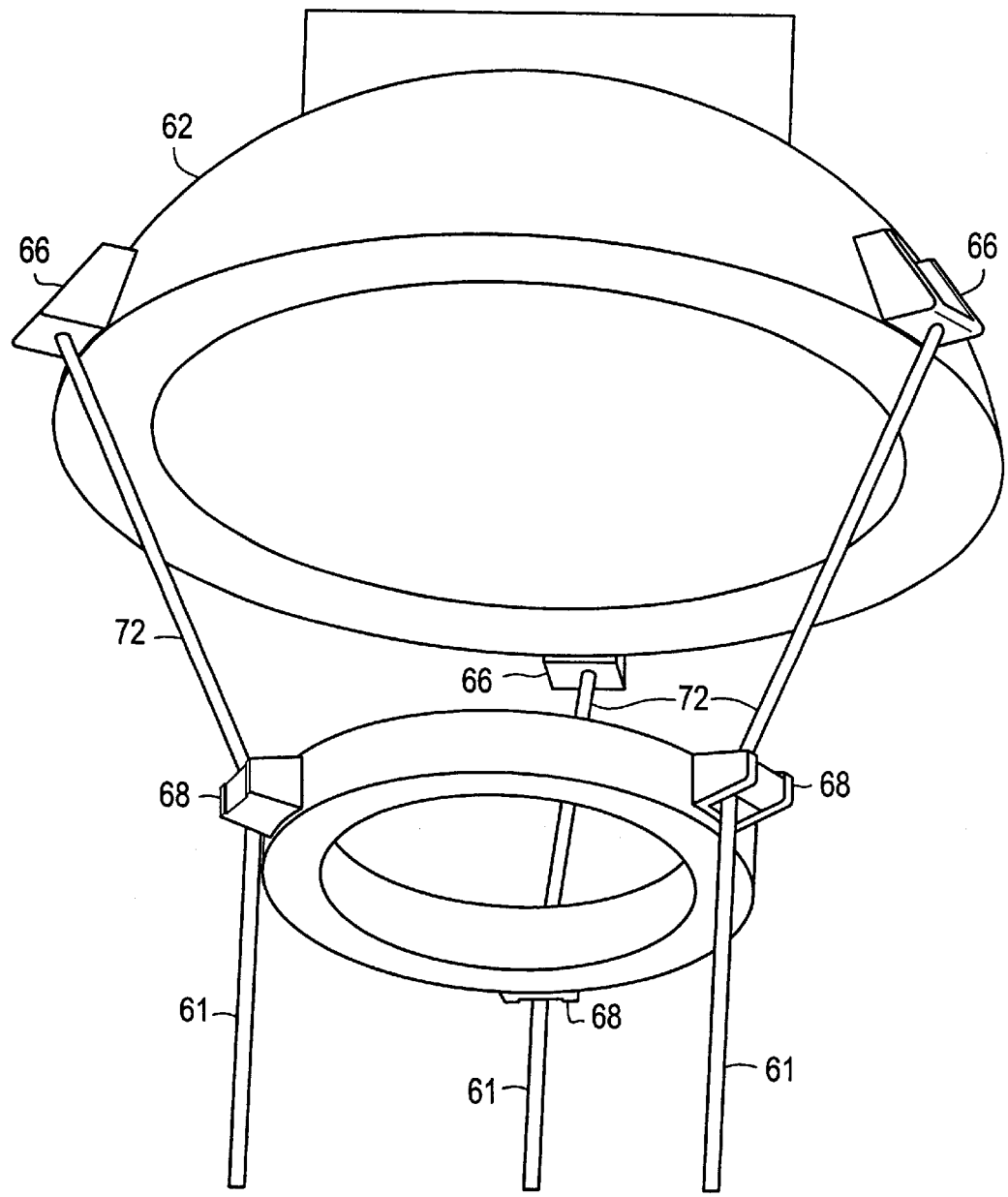
FIG. 15 shows a perspective view of a cup and bracket combination used to support a plurality of smart material artificial muscle actuators of the present invention.
Figure 16:
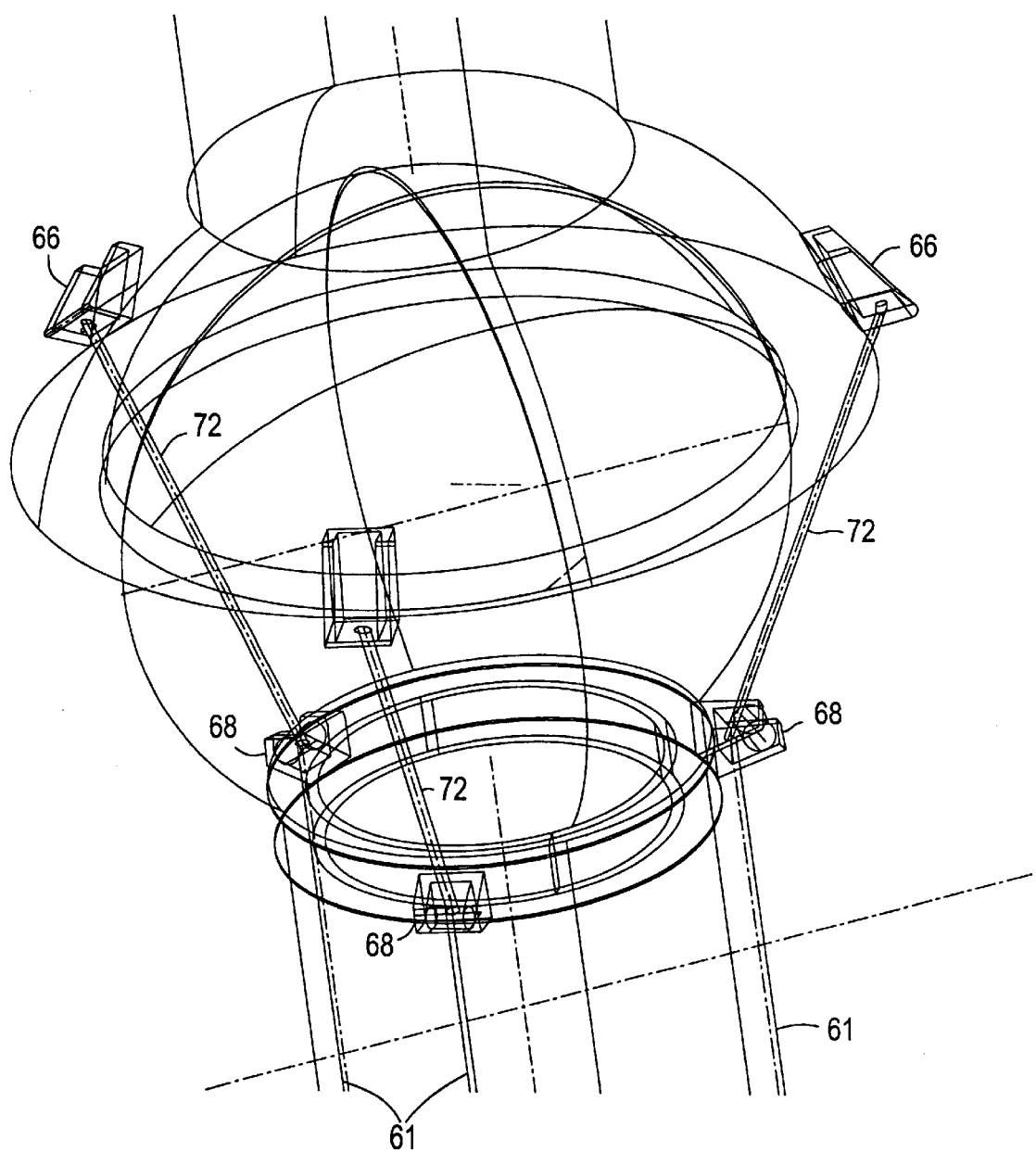
FIG. 16 shows a line drawing of the spherical joint of FIG. 14 showing placement of smart material artificial muscle wires thereon.

As specifically illustrated in FIGS. 15 and 16, cup 62 supports a plurality of brackets 66 around a periphery thereof Brackets 66 provide a mount for "tendons" 72 of SM muscles 61 on the outer perimeter of cup 62. Tendons 72 are preferably small Teflon-coated braided steel wires crimped onto each end of each smart material wire 61. The SM wire is itself crimped to a light braided metal "tendon" 72. Tendons 72 not only supply current to the SM muscle, but also isolate the SM muscle from any surface that could inhibit the smart material's performance.

Figure 17:
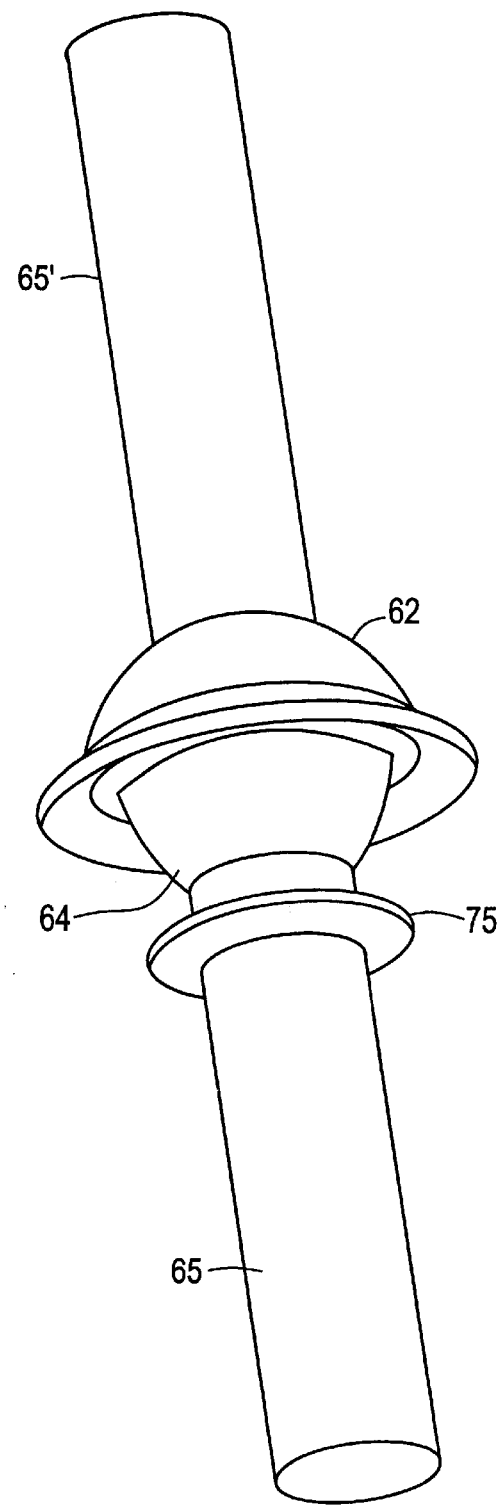
FIG. 17 shows a perspective view of an alternative spherical joint having a collar for attachment of smart material artificial muscle wires thereto.

SM muscles 62 are mounted along shaft 65 and attached via fastening elements such as anchor brackets 70 at a lower end of shaft 65 and roller brackets 68 at an opposed upper shaft end. The terminal end of tendon 72 passes through a mounting hole in bracket 66 while the primary tendon portion passes through a simple guide such as bracket 68 mounted to shaft 65 proximate ball portion 64. Bracket 68 may be directly mounted to shaft 65 or alternatively provided on a collar 75 which is fitted around shaft 65 directly below ball portion 64 (as shown in FIG. 17).

More than one SM wire can be assembled in the same direction, one near the other, to form a muscle. Bundling smart material wires together, similar to strands of muscle fiber, will increase the strength and power of the joint. An example of how muscle wires are placed within a joint to ensure accurate movement and agility is specifically shown in FIG. 16, wherein the placement of muscle wires 61 is predetermined according to the dynamic motion desired to be achieved by the joint and the dimensional constraints inherent in designing a unique prosthesis for each patient. Placement of bundles of SM wire on a rehabilitative device is determined according to the method described hereinabove.

EXAMPLE

Examples of muscle actuators tested using joint system 60 include nickel-titanium alloy wires having a diameter of 150-microns at an actuation temperature of 70° C. These wires have an average contraction of 6% with a current of 0.2 Amps at room temperature and can apply pull forces of approximately 250 g each.

The system electronics include a 300 MHZ Dell Pentium PC equipped with a Datel model PC-412 A/D and D/A converter board. Connected to this board is an interface box which contains the circuitry for an operational amplifier and position sensors. For the position sensing of a free end of the support shaft 65, there are two wire wound linear motion precision potentiometers mounted in coordination with the two planes of motion accomplished by this joint.

Initial testing of the 150-micron wires demonstrated that this system was capable of lifting approximately one pound. The range of motion of the joint was approximately 20° in all directions with the end point of the shaft tracing a circle radius of approximately 10". A displacement corresponding to an angle of approximately 20°, which was the limit of the ball-and-socket joint used, was attained. Slightly less displacement is obtained if a load is attached. However, bundling the wires increases the lifting capabilities of the arm. The antagonistic placement of the muscles makes it possible to have a short and uniform reaction time in every direction.

Figure 18:
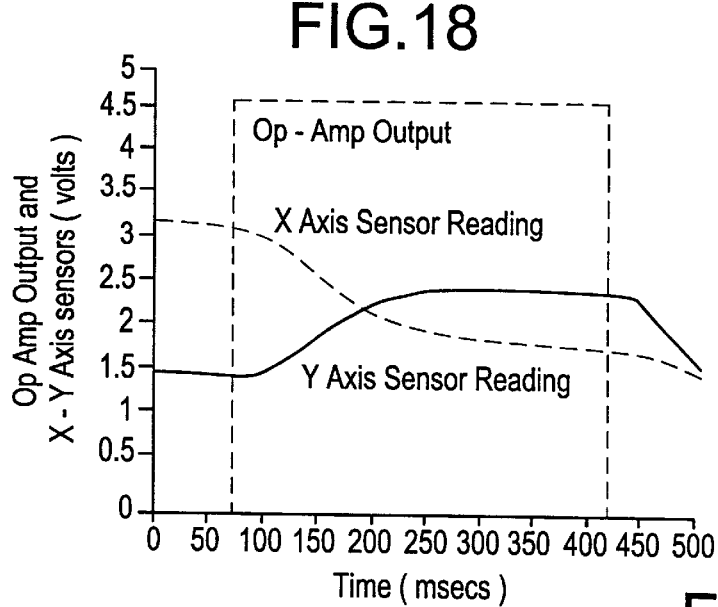
FIG. 18 shows illustrative actuation voltage and sensor readings for smart material artificial muscle wires used in a spherical prosthesis.
Figure 19:
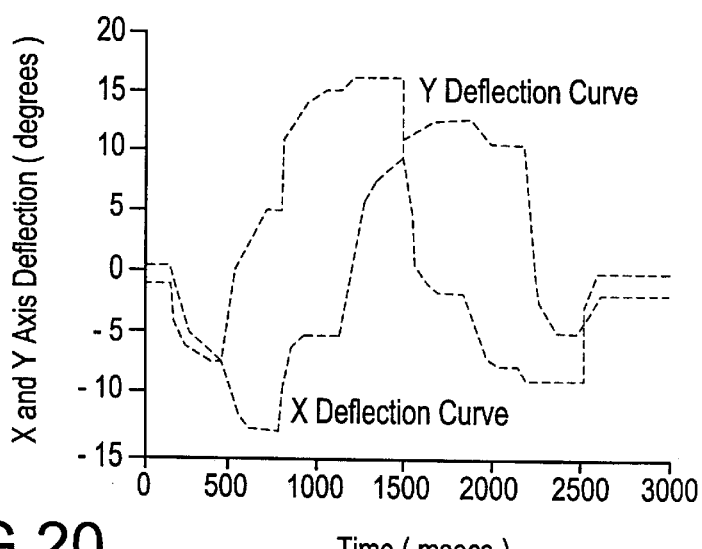
FIG. 19 shows an illustrative range of motion for smart material artificial muscle wires used in a spherical prosthesis.
Figure 20:
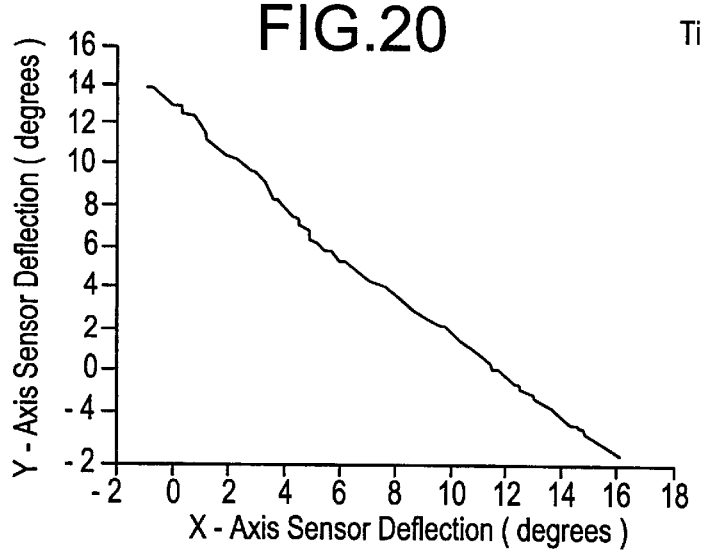
FIG. 20 shows an illustrative straight line motion in joint space for smart material artificial muscle wires used in a spherical prosthesis.
Figure 21:
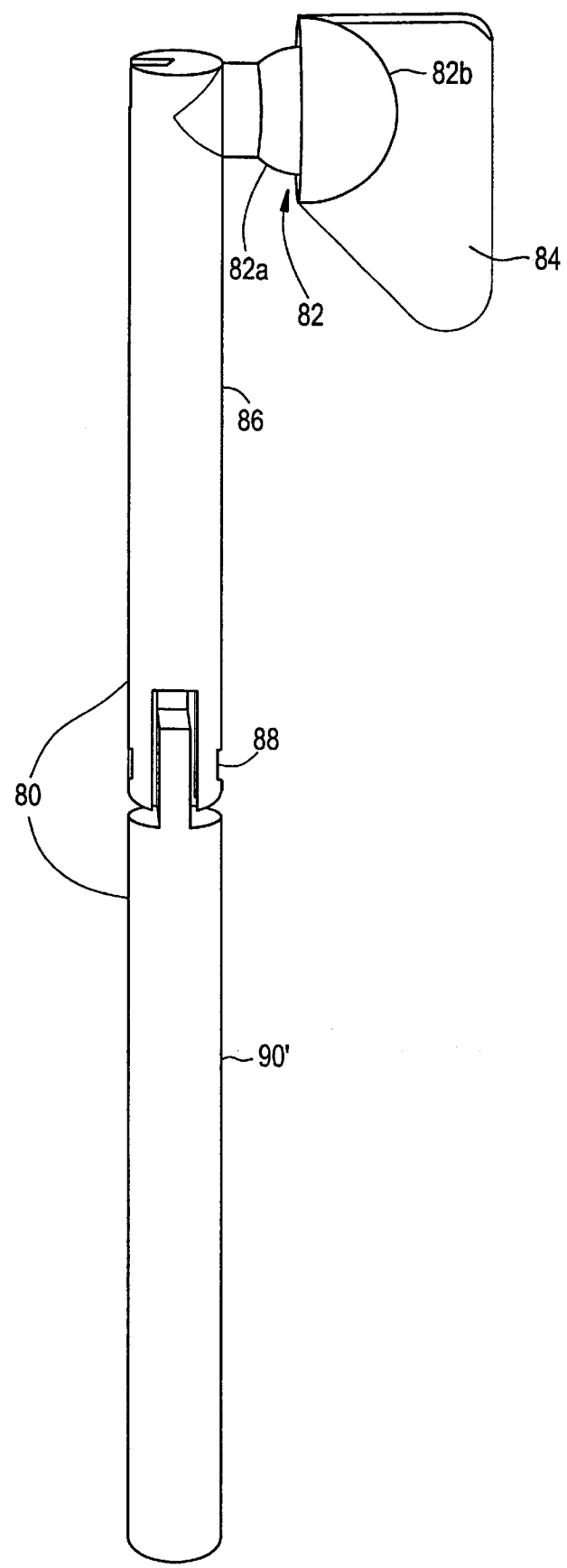
FIG. 21 shows an anterior view of a prosthetic arm constructed in accordance with the present invention.
Figure 22:
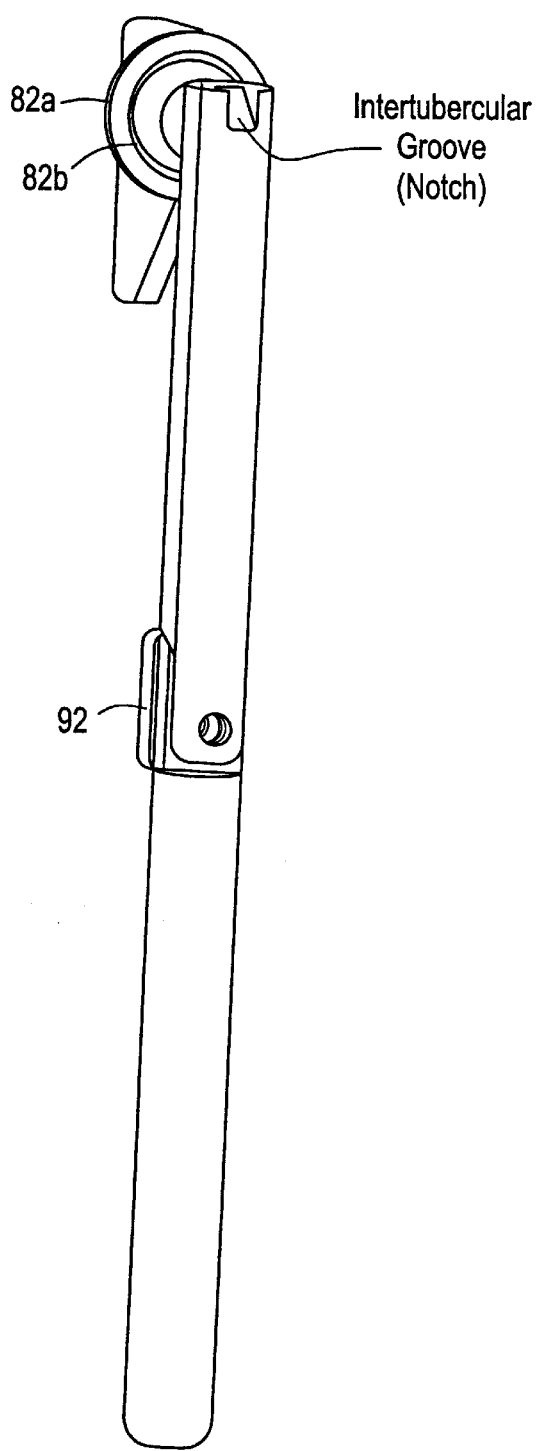
FIG. 22 shows a lateral view of the prosthetic arm of FIG. 21.

Some results obtained during open loop initial experiments of the shoulder prototype are shown in FIGS. 18–20. FIG. 18 displays actuation voltage sent to the SM wires (in this case, SMA wires) and the readings of the two position sensors in volts. These two sensors are placed in a vertical configuration relative to each other such that they are able to measure the joint angles around two perpendicular axes, labeled as X and Y. Initial voltage is measured at 75 milliseconds, and the time wherein maximum deflection of the smart material is realized is recorded at approximately 300 milliseconds. The smart material, therefore, has a reaction time of about 225 milliseconds.

FIG. 19 illustrates the ranges of motion of the joint when actuated by these shape memory alloy wires. It can be seen that at 1250 milliseconds, the angular deflection around the X axis is at approximately 0° and the maximum Y deflection is at about 17°.

FIG. 20 shows the spherical joint following a straight line in joint space. The initial configuration of the system is (x, y)=(14°, −1°) and the final configuration is at (−3°, 16°). The open loop control of the SM-actuated joint is very accurate as the joint closely follows a straight line in space. For this test the final point is reached in approximately 0.5 seconds.

Arm Prototype With Elbow

A prototype of a prosthetic arm 80 actuated by artificial muscles and adapted for securement to a patient is illustrated in FIGS. 21–24. The patient is able to control a multi-degree of freedom robot prosthesis and, at the same time, get force, moment and similar feedback information. The patient uses visual, haptic and auditory signals to control the prostheses through an (EMG) interface as described hereinbelow. The artificial limb is designed to be lightweight, compact and dexterous so as to mimic anatomical behavior and maintain a high lifting capability. Human skeletal and muscle names identify the assembly parts of arm 80.

A shoulder portion or scapula 84 interacts with humerus 86 to form a rotatable ball and socket joint 82. As particularly shown in FIG. 22, humerus 86 has an intertubular groove or notch 86a that provides an anchoring or support surface for artificial muscles thereon. Joint 82 includes a spherical head or ball portion 82a formed at an upper extremity of humerus 86 and a glenoid cavity or cup portion 82b integrated in scapula 84. Ball-and-socket joint 82 allows for three degrees- of-freedom, thereby mimicking actual motion of the human shoulder.

Arm 80 further includes ulna 90 hingedly affixed to humerus 86 at hinge joint 88. At an upper extremity of ulna 90 proximate hinge joint 88, an olecranon process or elbow 92 is defined to replicate actual elbow joint formation and function.

Figure 23:
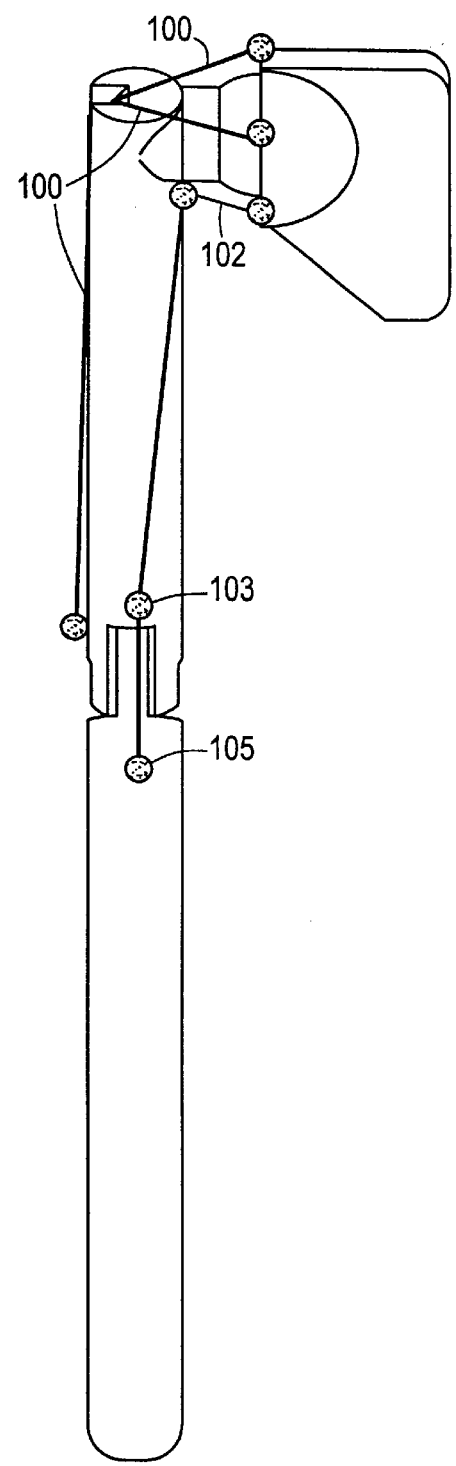
FIG. 23 shows an anterior view of the prosthetic arm of FIG. 21 showing placement of smart material artificial muscle wires thereon.
Figure 24:
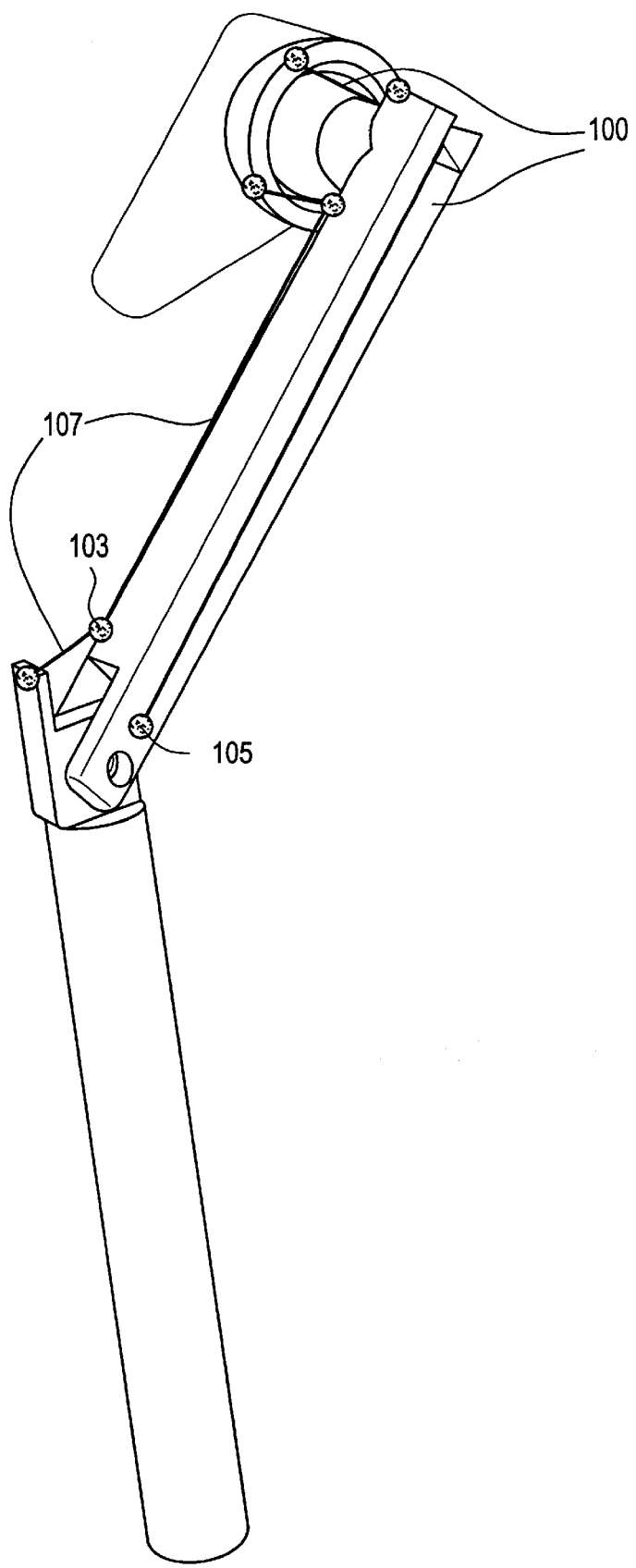
FIG. 24 shows a lateral view of the prosthetic arm of FIG. 23 showing placement of smart material artificial muscle wires thereon.
Figure 25:
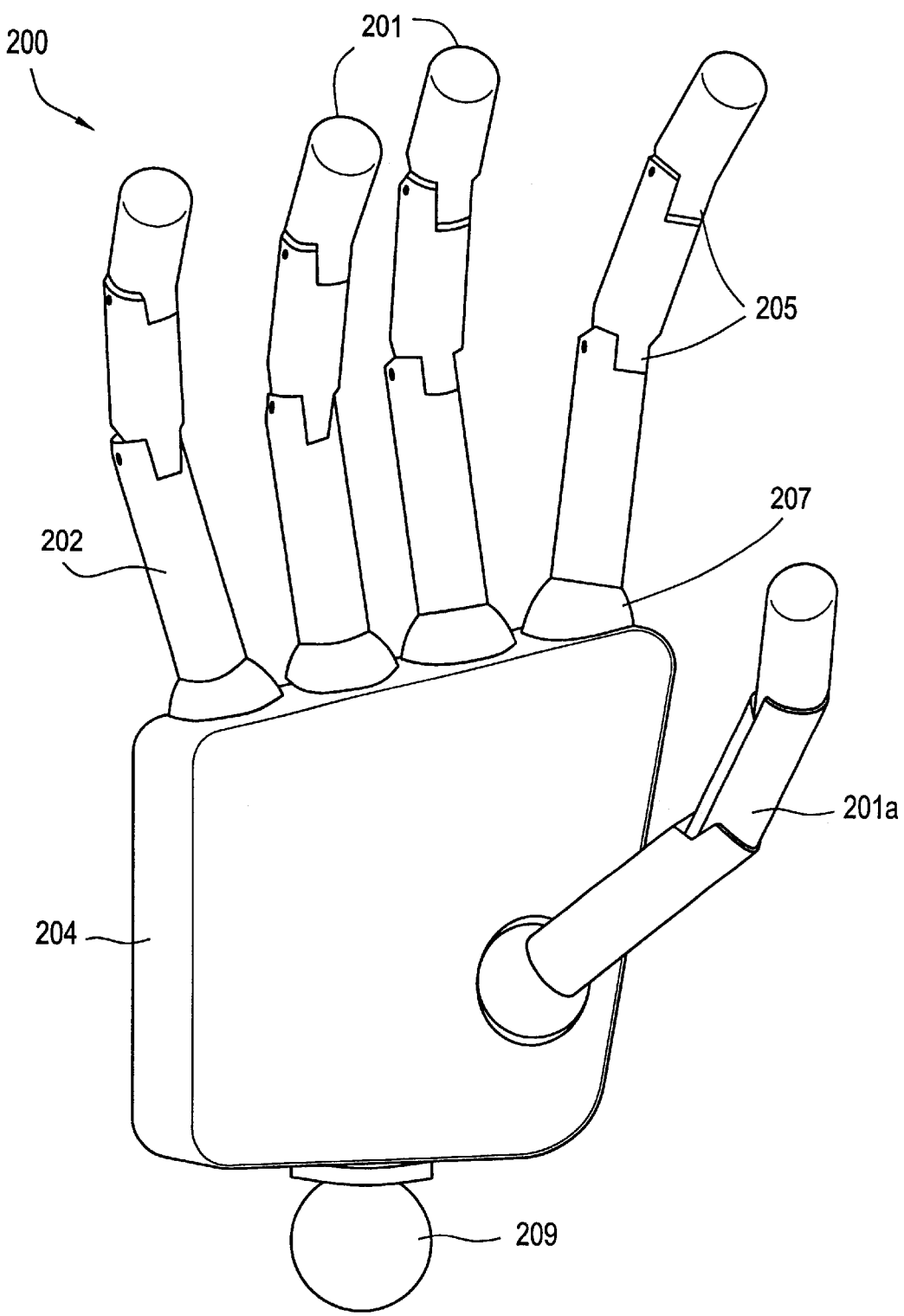
FIG. 25 shows an anterior view of a robotic hand constructed in accordance with the present invention.

Referring further to FIGS. 23 and 24, scapula 84, in conjunction with notch 86a and anchor 105, serves as an anchoring position for SM artificial muscle actuators such as deltoids 100, bicep 102 and tricep 107. These "muslces" are precisely defined to replicate motion of the elbow-hinged prosthetic arm in an anthropometrical manner. Positioning of the muscles is variable, however, placement of the actuators along arm 80 is dependent upon a variety of factors such as the proportions of the patient and the end function of the arm

Hand and Finger Prototype

A pair of five-fingered hand prototypes anticipated for use with the present invention are further shown in FIGS. 25–36. As particularly shown in FIGS. 25 and 26, a prosthetic hand 200 includes five appendages or fingers 201 assembles thereon. Hand 200 includes a palm 204 having a solid construction, with socket indentations 204a for placement of fingers 201 therein. Fingers 201, which are comprised of several links or phalanges 202, are connected to palm 204 by three-degree-of-freedom ball-and-socket joints 207, which will be restricted to two degrees of freedom. Thumb 201a will retain three-degree-of- freedom movement. Hand 200 connects with a corresponding arm (not shown) with a ball-and-socket joint 209.

Figure 26:
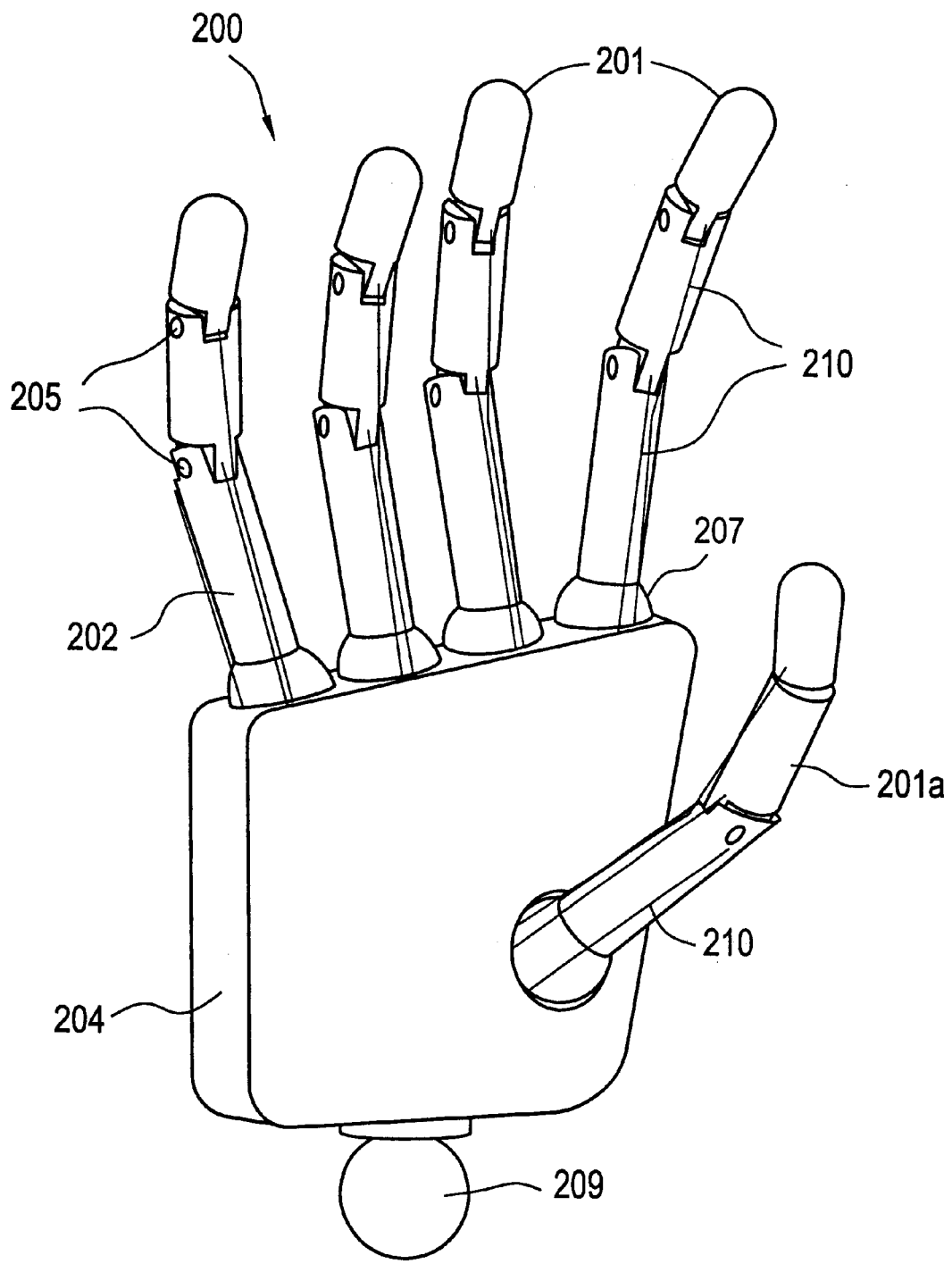
FIG. 26 shows the hand of FIG. 25 showing placement of smart material artificial muscle wires thereon.
Figure 27:
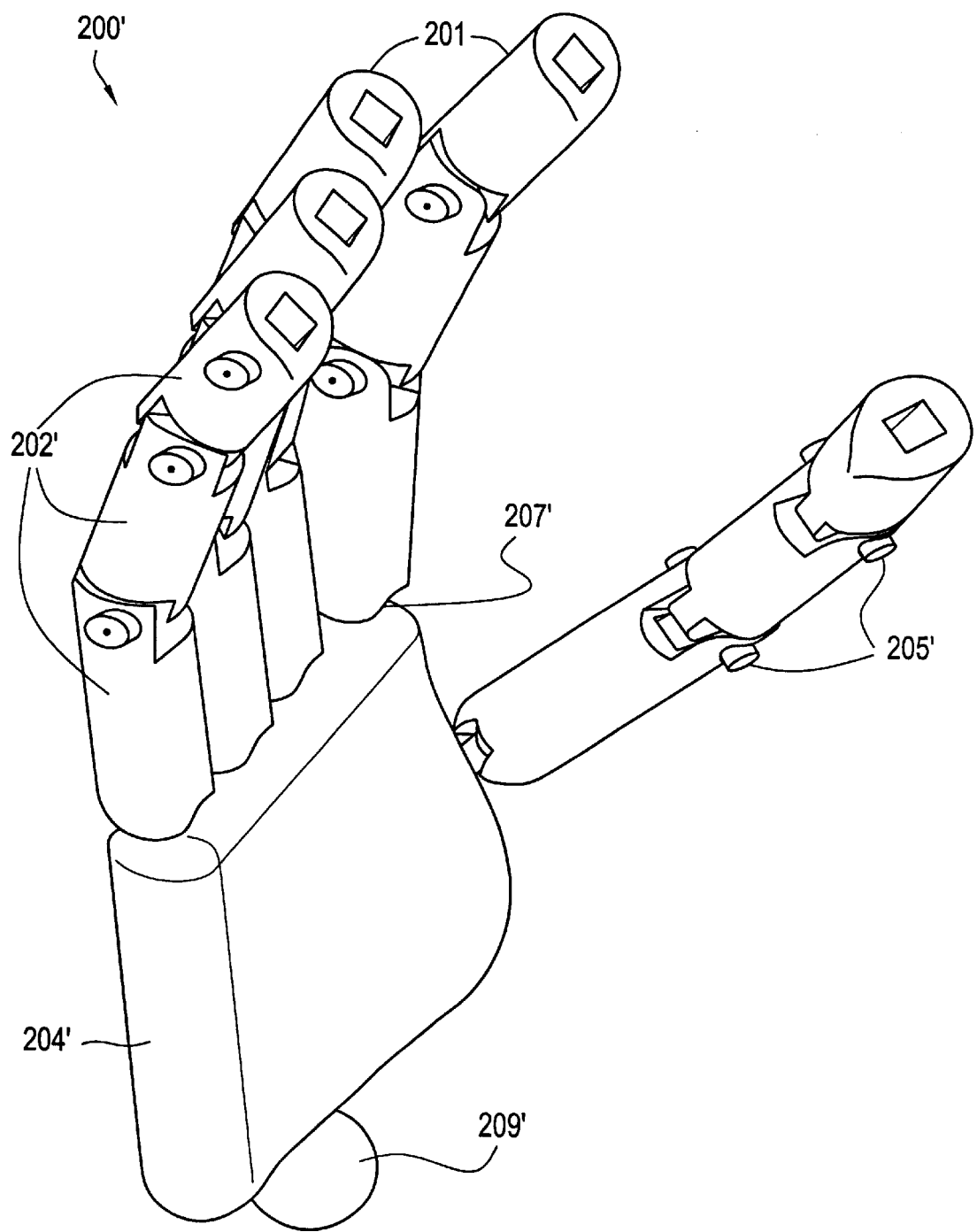
FIG. 27 shows an anterior view of a robotic assistive hand designed for interior mounting of smart material artificial muscle wires.
Figure 28:
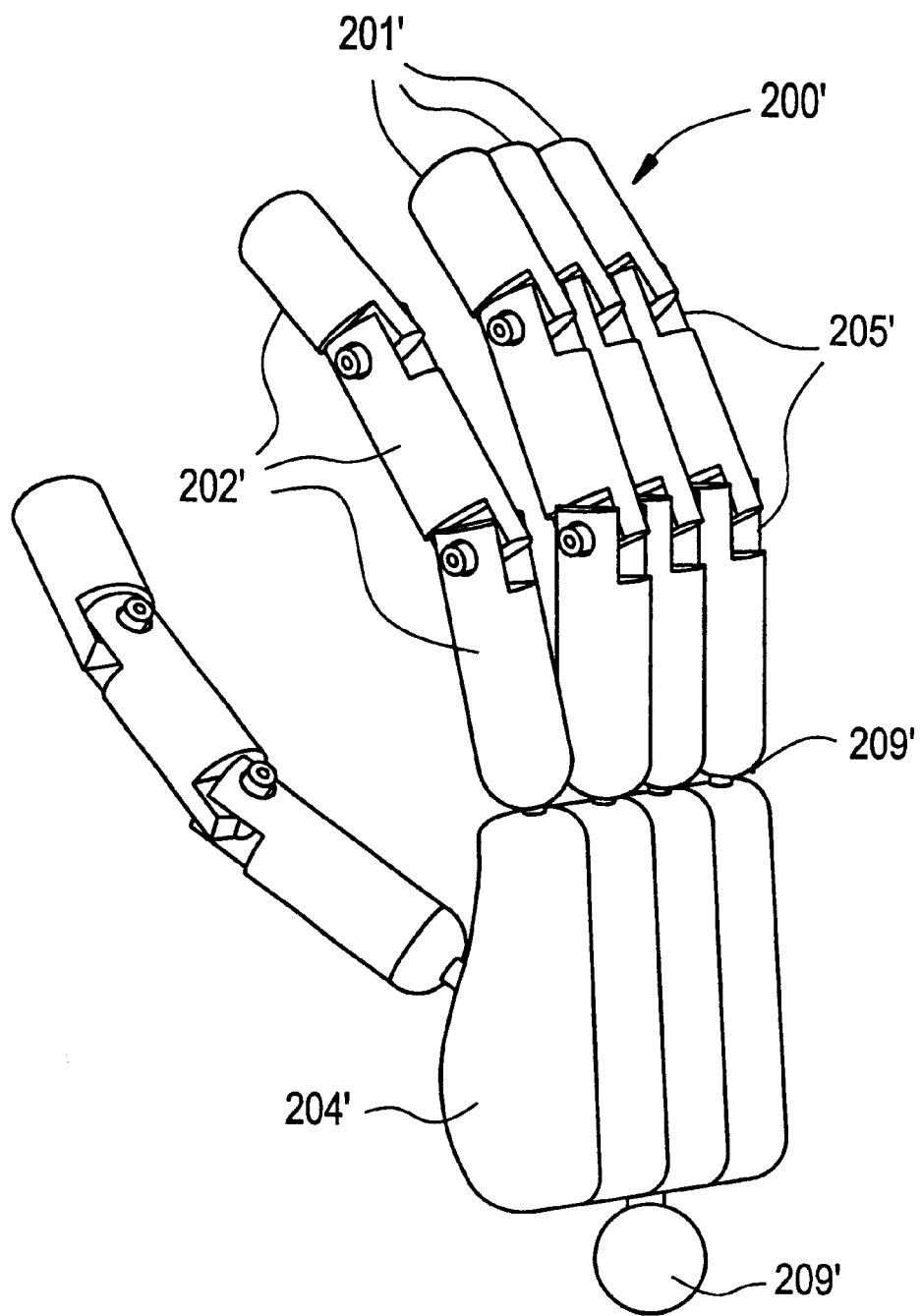
FIGS. 28 and 29 show a posterior view and a top view, respectively, of the robotic hand of FIG. 28.
Figure 29:
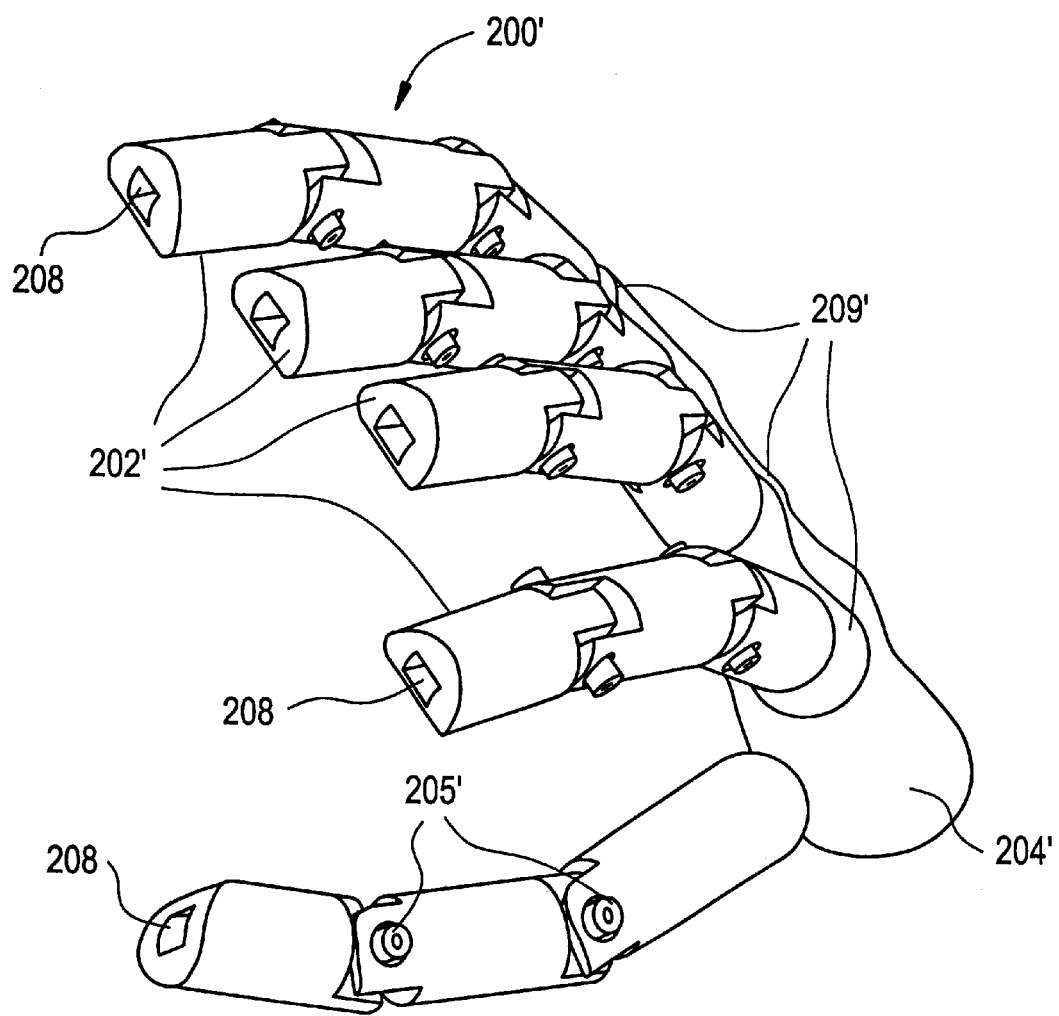
Figure 30:
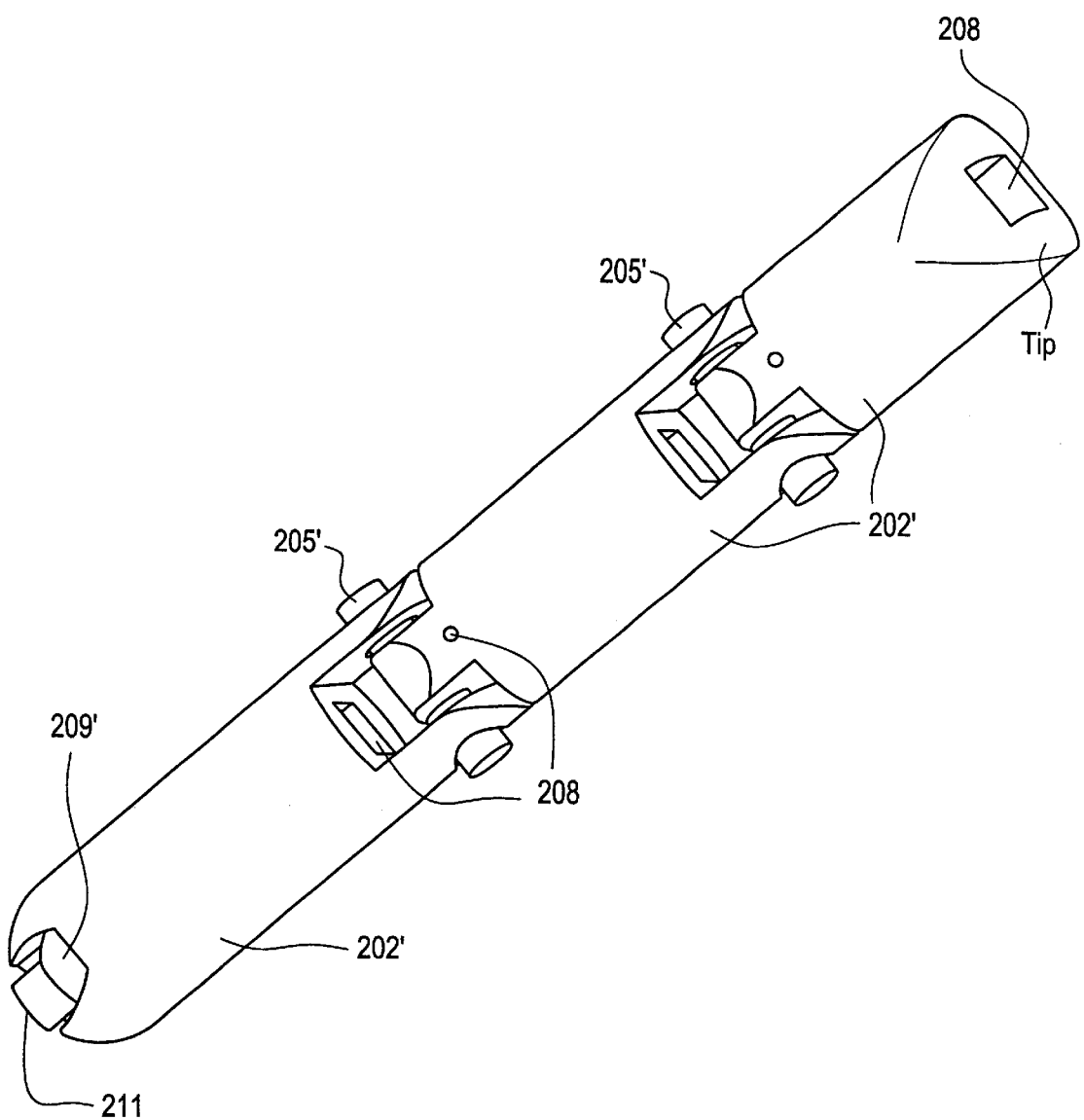
FIG. 30 shows a close perspective view of a robotic assistive finger of the hand of FIG. 28.
Figure 31:
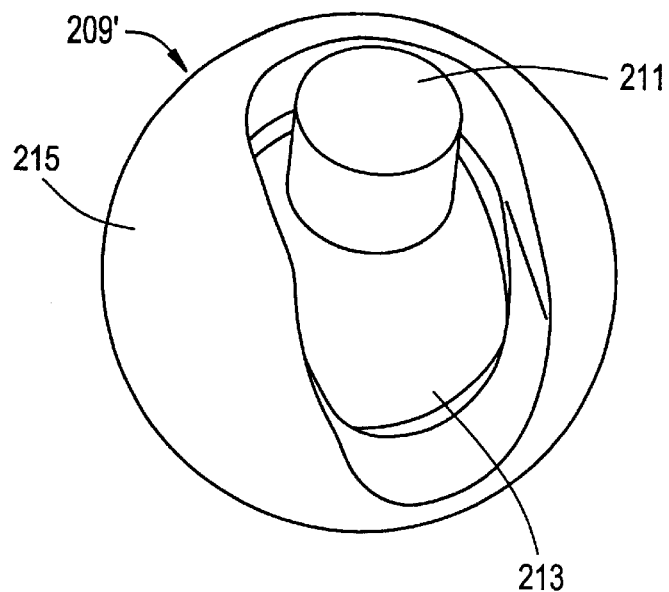
FIG. 31 shows a close perspective view of a spherical joint used for mounting to a hand as shown in FIG. 28.

Finger actuation is accomplished by a combination of cables and muscle wires as further shown in FIG. 26. The wire placement closely follow the flexor tendon attachments of the human hand. Actuation tendons 210, for instance, are anchored at ball and socket joints 207 to impart motion to a plurality of phalange hinge joints 205. Actuation of tendon 210 enables flexion and extension of fingers 202 for grasping and release of objects in a manner that replicates anatomical hand muscle movement.

Now referring to FIGS. 27–32, another robotic assistive hand design 200' is provided that allows for the assembly of all cables, wires, tendons, sensors and other components inside fingers 201' and palm 204'. Each finger 201' includes several links or phalanges 202' that are joined together by a revolute hinge joint 205' held together by a drift pin. (A preferred configuration of hinge joint 205' is particularly shown in FIG. 32). Fingers 201' are connected to palm 204' by a three degree-of-freedom ball-and-socket joint 207', which will be restricted to two degree-of-freedom, or connected by a ball rod end joint. The thumb will retain three degree-of-freedom movement. Hand 200' similarly connects with a corresponding arm (not shown) with a ball-and-socket joint 209', further shown in FIG. 31. As depicted, a ball portion 213 is rotatably supportable by a socket portion 215 to effect two degree-of-freedom movement. Ball portion 213 further provides an area 211 for attachment to palm 204'.

Much like the previous prosthetic hand embodiment, prosthetic hand 200' is actuated by a plurality of smart material artificial wire members affixed to hinge joints 205'. Upon closer view of a prosthetic finger 201' (shown in FIG. 30) and revolute joint 205' (shown in FIG. 32), a plurality of channels 208 are provided which enable mounting of smart material muscle actuators along an interior portion of the prosthetic hand structure. Hand and finger actuation is thereby accomplished by a combination of muscle wires threaded through the hand and fingers themselves. Again, wire placement closely follows the flexor tendon attachments of the human hand to impart flexion and extension to hinge joints 205'.

An actual prosthetic finger constructed in accordance with the present invention is further provided in FIGS. 33–34 (wherein like reference numerals are used for like parts). Finger 201' is a three-degree-of- freedom planar appendage actuated by a set of tendons 210 and artificial muscles IS 210a, all fabricated of smart materials such as SMA wires. Finger 201 ' includes a small three-linkage component having tendons 210 and muscle wires 210a affixed thereto.

Figure 32:
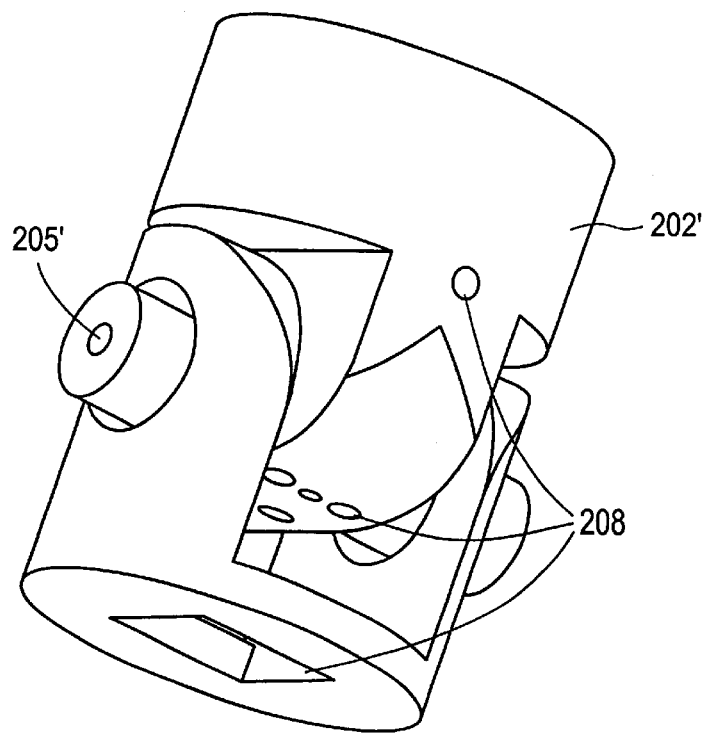
FIG. 32 shows a close perspective view of a revolute joint used in an assistive finger of FIG. 31.

Referring particularly to FIG. 34, the small three-linkage finger component is preferably made of a lightweight material such as aluminum including only revolute joints as shown in FIG. 32. These joints are machined well, with tiny ball bearings placed around the major axes to reduce friction in the joints. Thin braided tendons are connected distal to each joint and run through a small channel along the length of the bottom of the finger. The tendons are crimped to the SM muscle wire, and the muscle wire is thereafter crimped to another tendon. A thin plastic piece runs across the top of each joint to act as a spring to provide the recovery force needed to reshape the wire.

This type of assembly shows the placement of the tendons and muscle wires in relative position of the palm, wrist and forearm, for application as a prosthetic or orthotic device, space robot manipulator or other articulatable device.

Figure 35:
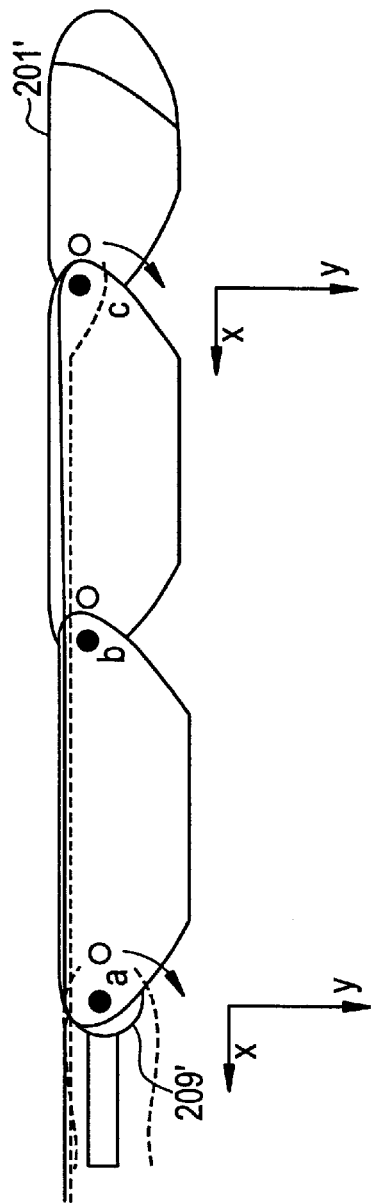
FIG. 35 shows a schematic of an articulated finger prototype with one possible method of link deflection.
Figure 36:
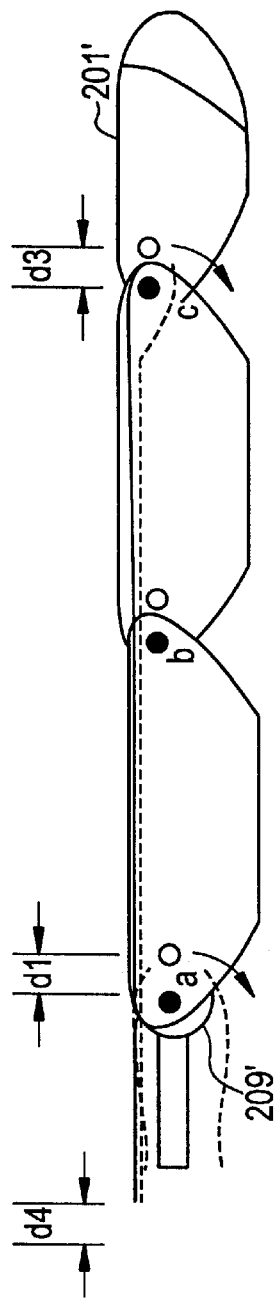
FIG. 36 shows a schematic of an articulated finger prototype with predetermined anchor placement of smart material artificial muscle wires from the pivot points for desired deflections.

Additionally, for a robotic assistive hand design FIG. 35 shows a schematic of an articulated finger prototype with one possible method of link deflection. FIG. 36 shows an additional schematic of an articulated finger prototype with predetermined anchor placement of smart material artificial muscle wires from the pivot points for desired deflections.

Design of Smart Orthoses Using SMA Actuators

The SM bundle artificial muscle actuators of the present invention can be used not only in powered prostheses but also in orthoses, due to their small size, low cost and large force capability. This assistive device can be used for active orthotics which offer greater flexibility of motion and a more versatile assistive device than current static orthoses. From the medical point of view, physical therapists and orthotists will have access to new therapeutic tools and equipment that will not only increase patients' comfort but also provide automatic monitoring of the patient performance via a patient-tool computer controlled force interaction. From the commercialization point of view, orthotics is a large market that provides the possibility for successful technology transfer of the novel devices.

Two examples of orthotic equipment that have been developed in accordance with the present invention are provided herein. These are an arm orthosis and a smart cervical orthosis, shown in FIGS. 37 and 38, respectively. As indicated hereinbefore, however, application of the present invention is not limited to the exemplary orthoses described herein. Individuals who have lost the ability to control an arm can greatly benefit from a comfortable, lightweight, easy to use robotic orthosis.

Figure 37:
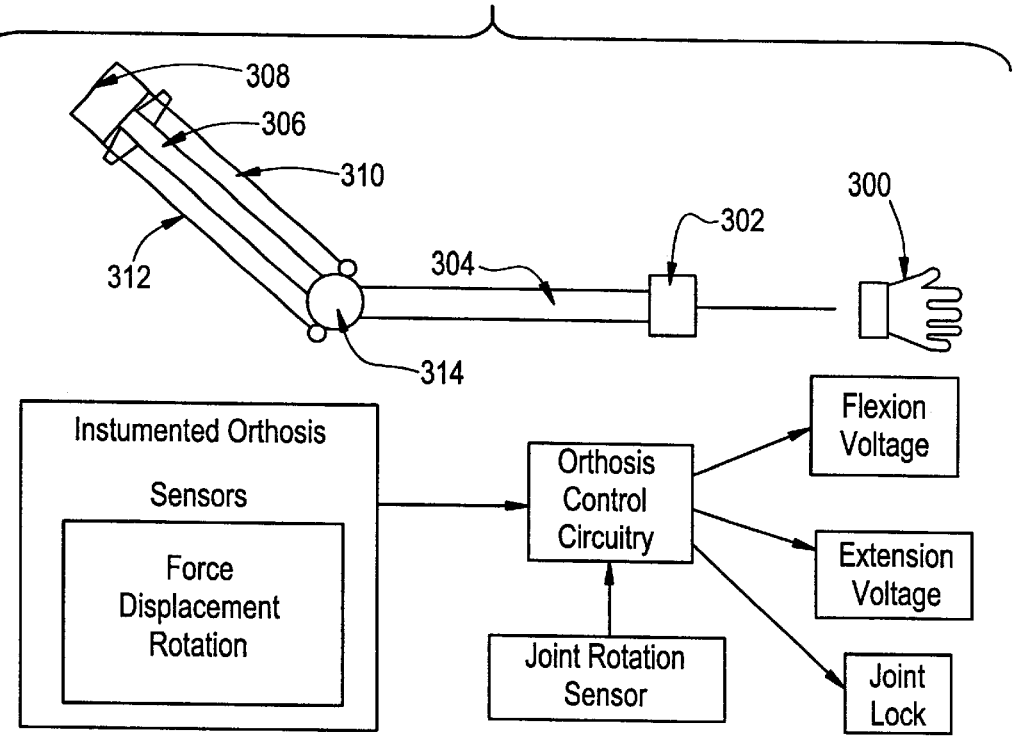
FIG. 37 shows a schematic of a smart arm orthosis of the present invention.

FIG. 37 shows a smart arm orthosis 300 having an instrumented anthropometrical member such as hand orthosis 301 at a free end thereof. Arm orthosis 300 includes a humerus 305 that incorporates a flexion smart material actuator 310 and an extension smart material 312 therein proximate orthosis command circuitry 308. (The configuration of flexion wire bundle 310 and extension wire bundle 312 is similar to that shown in FIG. 8, described hereinabove with respect to a prosthetic elbow.) Arm orthosis 300 further includes a radius section 304 hingedly connected to an elbow joint 314. An automatic lock may be incorporated into elbow joint 314 to conserve power when positioning of arm 300 or hand 301 is not required. A hand-arm interface 302 is also accommodated between radius section 304 and hand orthosis 301.

As depicted in FIG. 37a, the patient communicates with arm orthosis 300 via another instrumented device that is worn on a part of the body that the user can control (described in detail further hereinbelow). For example, if the user is able to make small, repetitive motions with the wrist, then an instrumented orthosis can be worn on the hand and wrist that detects and measures force, displacement, rotation and other environmental stimuli at interface 302 and transmits the detected information to command circuitry 308. Command circuitry 308 processes the information and simultaneously issues commands for flexion or extension of the limb while monitoring joint rotation. Antagonistic SM bundles 306 and 312 are analogous to the bicep and tricep muscles to provide the power for flexion and extension.

Figure 38:
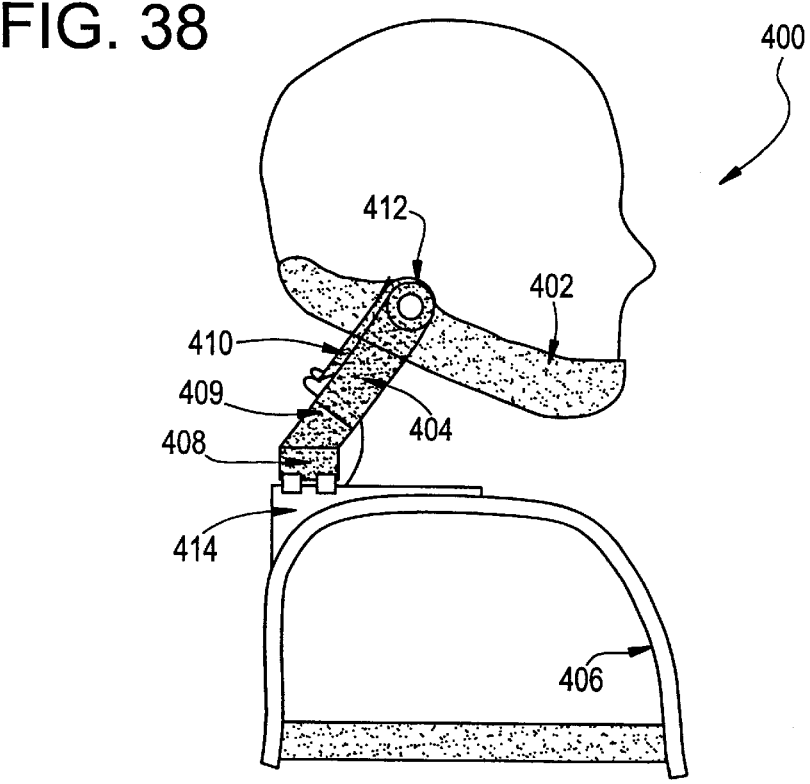
FIG. 38 shows a schematic of a smart cervical orthosis of the present invention.

In FIG. 38, a smart cervical orthosis device 400 is shown orthosis 400 is particularly adapted for individuals who have lost the ability to control the orientation of the neck with respect to the torso. Access to orthosis 400 is facilitated by access hinge 409 on neck support 404. Hinge 409 allows head support 402 to unlock into two parts for easy donning.

When the two parts are joined again, head support 402 comfortably cradles the user's head and pivots about an axis 412 that corresponds to the natural tilt of the human head (the "Azimuth Pivot"). SM actuators 410 connected to neck support 404 and axis 412 provide power to tilt the head.

Rotation of the user's neck with respect to the torso is accomplished by a cervical rotation transport mechanism 408 (CRTM). This mechanism translates in a circular path whose center of curvature corresponds to the anatomical rotation axis of the neck. The entire orthosis is supported by a comfortable torso brace 406 similar to that of modem stationary cervical orthoses.

The basic operation of smart cervical orthosis 400 is similar to that of smart arm orthosis 300. The individual can communicate with the orthosis using an input device that is best suited to the individual's ability. Appropriate command circuitry will process the user's input and then issue control signals to the Azimuth SM actuator and the CRTM for the desired positioning of the head.

All of the above described assistive devices (prostheses and orthoses) are equipped with very small linear transducers (not shown) that will provide real time measurement of the muscle displacements. These measurements will aid in the calculation of the joint positions necessary for closed loop control schemes.

The system electronics that are-used to control the motion of devices constructed in accordance with the present invention include a computer system, a digital to analog converter, amplifiers and a power supply. The system can operate in open loop mode where no feedback of the joint motion is obtained, or in closed loop mode. In closed loop mode, the joint's position and orientation can be either estimated by models by measuring the voltage applied to the muscles or by using small linear encoders to measure accurately the length of the muscle wire. The latter is considered to be the most efficient method to control these systems.

Personal Portable Control of Smart Material Actuated Assistive Devices

The assistive devices described and shown herein are preferably controlled using electromyographic (EMG) signals obtained from the patient's residual muscles along with a system of sensors that detect environmental stimulation on the device and provide corresponding feedback signals to the command circuitry. Low level command interface is performed using the EMG signals. Higher level control of the arm, i.e., decision making, is accomplished by the patient's cognitive skills using sensory feedback obtained from the system sensors. The patient's own visual capabilities will be used to supervise the position control of the arm and generate the necessary EMG signals. It is expected that adaptive control gains based on environmental and payload changes will permit the patient to better perform a large variety of tasks, vastly increasing the feeling of physical and psychological comfort in the patient.

Figure 39:
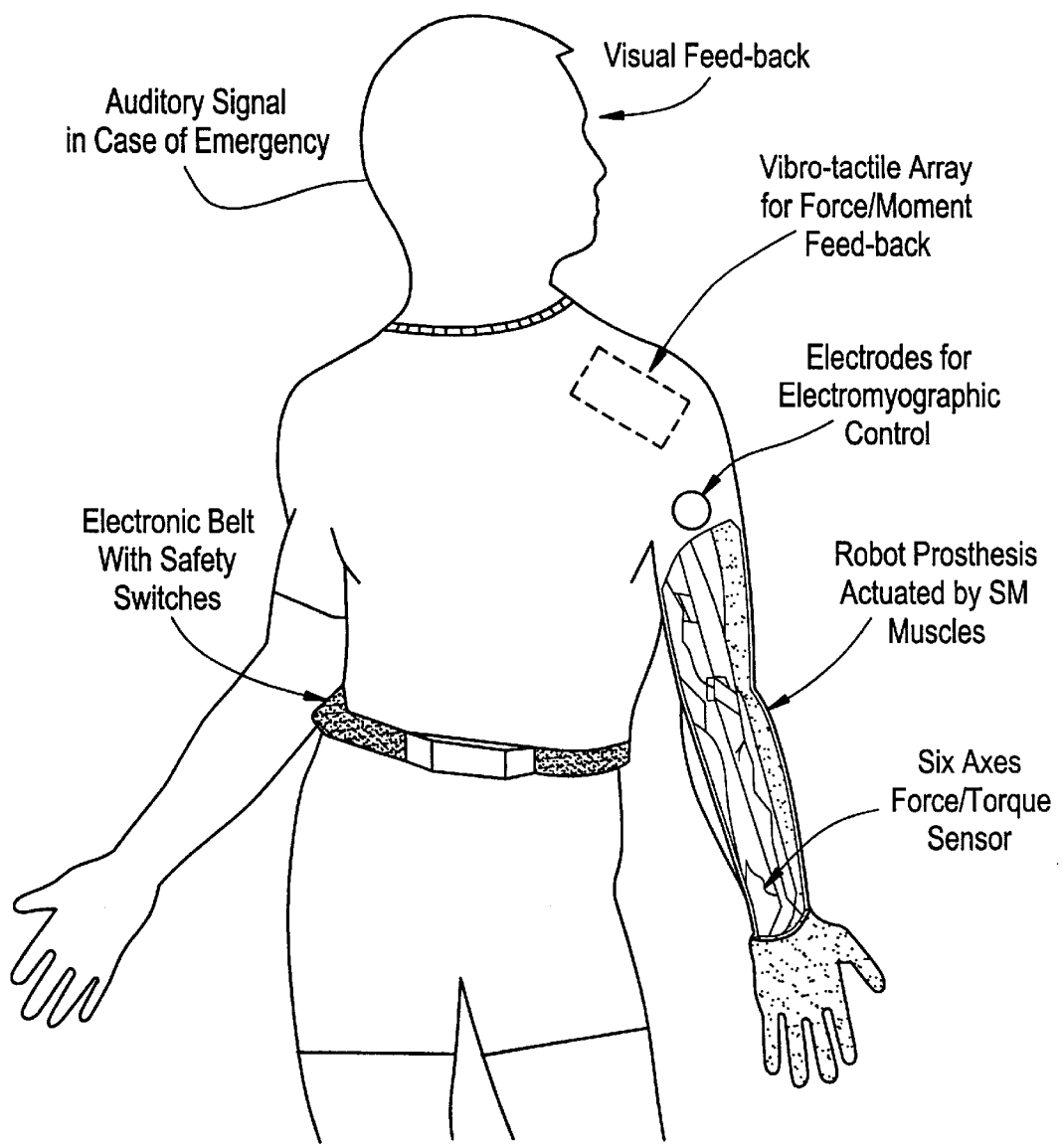
FIG. 39 shows a portable device worn by a patient for control of a smart material actuated device of the present invention.

As illustrated in FIG. 39, the control electronics and power are preferably installed on a lightweight portable device worn by the patient. An example of such a portable device is belt 500 as shown in FIG. 39. Belt 500 is a self-contained system for control of and detection of environmental stimuli on robotic arm 502.

Belt 500 includes a micro-controller board along with an analog-to-digital (A/D) board and a digital-to-analog (D/A) board. The micro-controller processes software operations such as the control of analog signals to arm 502 and the detection and processing of sensory signals therefrom. The A/D portion of the circuitry converts sensory inputs from a plurality of system sensors such as proximity detectors, tactile sensors (i.e. vibro-tactile array 52 as shown in FIG. 39 and described hereinabove with respect to FIG. 12), accelerometers and linear encoders integrated into the prosthetic arm. The D/A portion of the circuitry serves as the control output to drive the operational amplifiers that will actuate the muscles within the arm.

Belt 500 further includes components such as a double latch safety shut-off switch (which, when engaged, will shut off all power to the arm), a number pad and a plurality of status indicators (such as LEDs) that provide the patient with the current operational status of the arm. Additionally the batteries which power the entire system, are also located here.

Conclusion

The examples provided in this disclosure emulate human skeletal structures via actuation with smart material artificial muscles. SM artificial muscle actuators decrease overall weight since they weigh even less than the power connection wires of a servo motor itself, and they perform with the same capability as the servo does. It is shown that these systems can exhibit relatively large motions and their use is possible for artificial limbs. The methods and prototypes presented in this disclosure show that smart material muscles can be used as actuators in artificial human limbs. However, a multitude of design and applications, both medical and non-medical, can be realized with the teachings of the present invention.

The reaction time of some smart materials is not the same when the wire contracts as when it extends, due to the inherent non-linear behavior of the material. Placement of antagonistic smart material in the design of the artificial members will resolve this problem. This antagonistic smart material feature emulates human anatomy, so that smart materials work together to provide a member having the same behavior during extension as during contraction. To avoid overloading and breaking of the smart materials, assistive devices can be equipped with smart material wire arrangements which coordinate the synergies of smart materials. In addition, springs can be added to increase the smart material compliance. Some smart materials have limited life cycles. In these cases, use of a modular smart material design system allows quick and easy replacement in the assistive device.

The present invention will have a wide impact on the biomedical, biomechanical, rehabilitative, prosthetic and orthotic engineering fields. It will lead to new devices, methods, and techniques to help disabled persons perform dexterous and fine tasks and assist medical specialists in accomplishing fast and successful treatments. Robotic systems will be implemented to perform surgical procedures such as knee arthroplasty, neurosurgery, eye surgery, and endoscopic diagnostic and surgical interventions. In addition, robotic and mechatronic technologies will be further implemented to design and control rehabilitation systems as assistive devices for people with disabilities and to develop automated home health care systems.

Various changes to the foregoing described and shown methods and corresponding structures would now be evident to those skilled in the art. Accordingly, the particularly disclosed scope of the invention is set forth in the following claims.

What is claimed is:

1. A kinetic prosthesis actuated by artificial muscles providing increased dexterity and agility of an artificial limb, said prosthesis comprising:

an articulated support member releasably mounted to a patient in signal communication with said patient's residual muscle and having a free end responsive to electromyographic signals communicated thereby, said support member having a plurality of artificial muscles attached thereto, said artificial muscles comprising smart materials; and command circuitry in electrical communication with said residual muscles for communicating said electromyographic signals to said artificial muscles so as to effect anthropometrical movement of said articulated support member;

said artificial muscles being in electrical communication with said command circuitry such that when signals are transmitted to said command circuitry, said artificial muscles respond thereto for effecting movement of said articulated support.

2. The prosthesis of claim 1 wherein said artificial muscles comprise a bundle of elongate elements.

3. The prosthesis of claim 2 wherein said elements are selected from the group of artificial muscle configurations consisting of wires, ribbons, sheets and springs.

4. The prosthesis of claim 2 wherein said elements are mechanically connected in spaced parallel relation to one another.

5. The prosthesis of claim 4 wherein said elements are arranged electrically in a combination of series and parallel current paths.

6. The prosthesis of claim 1 wherein said artificial muscles are selected from the group of smart materials consisting of electrostrictive polymers, electroactive polymers, conductive polymers, electrostatic devices, piezoelectric polymers, mechano-chemical polymers and gels, shape memory polymers and shape memory alloys.

7. The prosthesis of claim 1 further comprising a detector system for detecting environmental stimuli sensed by said articulated support member and for producing detection signals in response thereto, and for transmitting said detection signals to said command circuitry through said artificial muscles.

8. The prosthesis of claim 7 wherein said system includes a plurality of sensors mounted on said articulated support member for detecting said environmental stimuli.

9. The prosthesis of claim 8 wherein said sensors are selected from the group of sensors consisting of force sensors, torque sensors, tactile sensors, thermal sensors, accelerometers and proximity detectors.

10. The prosthesis of claim 9 wherein said sensors produce detection signals corresponding to said environmental stimulation and transmit said detection signals to said command circuitry.

11. The prosthesis of claim 8 further comprising a portable device in electrical communication with said command circuitry.

12. The prosthesis of claim 11 wherein said portable device includes a belt wearable by said patient having a microcontroller therewithin for control of said member movement.

13. The prosthesis of claim 11 wherein said portable device includes circuitry for converting sensory inputs from said sensors into detection signals corresponding to said environmental stimulation.

14. The prosthesis of claim 1 wherein said articulated support member free end includes an anthropometrical element defined thereat.

15. The prosthesis of claim 14 wherein movement of said anthropometrical element is effected by said artificial muscles.

16. A method of effecting movement in an artificial limb wherein said limb is in signal communication with electromyographic signals obtained from a patient's residual muscles, said method comprising the steps of:

providing an articulated support member releasably mounted to said patient in signal communication with said patient's residual muscles, said member having at least one joint with a joint axis defined therethrough and further having a free end responsive to electromyographic signals communicated thereby;

attaching a plurality of artificial muscles comprising smart materials to said articulated support member so as to effect movement of said member corresponding to contraction or expansion of said artificial muscles; and providing command circuitry in electrical communication with said residual muscles for communicating said electromyographic signals to said artificial muscles so as to effect said member movement;

said artificial muscles being in electrical communication with said command circuitry such that transmission of signals to said command circuitry effects movement of said member.

17. The method of claim 16 wherein said artificial muscles comprise a bundle of elongate elements.

18. The method of claim 17 wherein said elements are selected from the group of artificial muscle configurations consisting of wires, ribbons, sheets and springs.

19. The method of claim 17 further comprising the step of mechanically connecting said elements in spaced parallel relation to one another.

20. The method of claim 19 further comprising the step of arranging said elements electrically in a combination of series and parallel current paths.

21. The method of claim 20 further comprising the step of applying a voltage to said elements to effect a change in length thereof.

22. The method of claim 16 wherein said artificial muscles are selected from the group of smart materials consisting of electrostrictive polymers, electroactive polymers, conductive polymers, electrostatic devices, piezoelectric polymers, mechano-chemical polymers and gels, shape memory polymers and shape memory alloys.

23. The method of claim 16 further comprising the step of determining a fixed attachment point for said artificial muscles.

24. The method of claim 23 wherein said attachment step is effected proximate said joint axis to enable large angular movements of said member.

25. The method of claim 23 further comprising the step of folding at least one of said artificial muscles in an overlapping configuration along a length of said articulated support member.

26. The method of claim 16 further comprising the step of providing a system for detecting environmental stimulation of said articulated support member and producing corresponding detection signals in response thereto, and for transmitting said detection signals to said command circuitry.

27. The method of claim 26 wherein said system includes a plurality of sensors mounted on said articulated support member to detect environmental stimulation thereof.

28. The method of claim 27 wherein said sensors are selected from the group of sensors consisting of force sensors, torque sensors, tactile sensors, thermal sensors, accelerometers and proximity detectors.

29. The method of claim 27 wherein said sensors produce said detection signals to correspond to said environmental stimulation and transmit said detection signals to said command circuitry.

30. The method of claim 29 further comprising the step of providing a portable device in electrical communication with said command circuitry.

31. The method of claim 30 wherein said portable device includes a belt worn by said patient and having a microcontroller therewithin for controlling movement of said articulated support member.

32. The method of claim 30 wherein said portable device includes circuitry for converting sensory inputs from said sensors into said detection signals.

33. An assistive device actuated by artificial muscles which provides increased dexterity and agility of an artificial or dysfunctional limb, comprising:

an articulated member having at least one joint pivotable about a corresponding joint axis and having a plurality of artificial muscles comprising smart materials affixed thereto wherein said artificial muscles are in signal communication with a system of sensors mounted on said member, said sensors detecting environmental stimulation of said member and producing detection signals corresponding to said stimulation, said sensors further transmitting said detection signals to command circuitry in electrical communication with said artificial muscles so as to effect anthropometrical movement of said member in response thereto.

34. The device of claim 33 wherein said artificial muscles are fabricated from at least one bundle of elongate elements.

35. The device of claim 34 wherein said elements are selected from the group of artificial muscle configurations consisting of wires, ribbons, sheets and springs.

36. The device of claim 34 wherein said elements are mechanically connected in spaced parallel relation to one another between a pair of end plates.

37. The device claim 36 wherein said elements are arranged electrically in a combination of series and parallel current paths.

38. The device of claim 37 wherein a voltage is applied to said elements to effect a change in length thereof.

39. The device of claim 33 wherein said artificial muscles are selected from the group of smart materials consisting of electrostrictive polymers, electroactive polymers, conductive polymers, electrostatic devices, piezoelectric polymers, mechano-chemical polymers and gels, shape memory polymers and shape memory alloys.

40. The device of claim 33 wherein said artificial muscles are fixed proximate said joint axis to enable large angular movements of said member.

41. The device of claim 33 wherein at least one of said artificial muscles is folded in an overlapping configuration along a length of said member.

42. The device of claim 33 wherein said sensors are selected from the group of sensors consisting of force sensors, torque sensors, tactile sensors, thermal sensors, accelerometers and proximity detectors.

43. The device of claim 33 further comprising a portable device in electrical communication with said command circuitry.

44. The device of claim 43 wherein said portable device includes a belt worn by said patient and having a microcontroller therewithin for control of said member movement.

45. The device of claim 43 wherein said portable device includes circuitry for converting sensory inputs from said sensors into said detection signals.

46. A method of effecting movement in an artificial limb wherein said limb is in signal communication with electromyographic signals obtained from a patient's residual muscles, said method comprising the steps of:

providing an articulated support member releasably mounted to said patient in signal communication with said patient's residual muscles, said member having at least one joint with a joint axis defined therethrough and further having a free end responsive to electromyographic signals communicated thereby;

attaching a plurality of artificial muscles comprising smart materials to said articulated support member at a location proximate said joint axis so as to enable large angular movements of said member corresponding to contraction or expansion of said artificial muscles; and providing command circuitry in electrical communication with said residual muscles for communicating said electromyographic signals to said artificial muscles so as to effect said member movement;

said artificial muscles being in electrical communication with said command circuitry such that transmission of signals to said command circuitry effects movement of said member.

47. The method of claim 46, wherein said artificial muscles are selected from the group of smart materials consisting of electrostrictive polymers, electroactive polymers, conductive polymers, electrostatic devices, piezoelectric polymers, mechano-chemical polymers and gels, shape memory polymers and shape memory alloys.

48. The method of claim 46, further comprising the step of folding at least one of said artificial muscles in an overlapping configuration along a length of said articulated support member.

49. A method of effecting movement in an artificial limb wherein said limb is in signal communication with electromyographic signals obtained from a patient's residual muscles, said method comprising the steps of:

providing an articulated support member releasably mounted to said patient in signal communication with said patient's residual muscles, said member having at least one joint with a joint axis defined therethrough and further having a free end responsive to electromyogrpahic signals communicated thereby;

attaching a plurality of artificial muscles comprising smart materials to said articulated support member so as to effect movement of said member corresponding to contraction or expansion of said artificial muscles;

folding at least one of said artificial members in an overlapping configuration along a length of said articulated support member; and providing command circuitry in electrical communication with said residual muscles for communicating said electromyographic signals to said artificial muscles so as to effect said member movement;

said artificial muscles being in electrical communication with said command circuitry such that transmission of signals to said command circuitry effect movement of said member.

50. The method of claim 49 further comprising the step of providing a system for detecting environmental stimulation of said articulated support member and producing corresponding detection signals in response thereto, and for transmitting said detection signals to said command circuitry.

51. The method of claim 50 wherein said system includes a plurality of sensors mounted on said articulated support member to detect environmental stimulation thereof.

52. The method of claim 51 wherein said sensors produce said detection signals to correspond to said environmental stimulation and transmit said detection signals to said command circuitry.

53. The method of claim 52 further comprising the step of providing a portable device in electrical communication with said command circuitry.

54. An assistive device actuated by artificial muscles which provides increased dexterity and agility of an artificial or dysfunctional limb, comprising:

an articulated member having at least one joint pivotable about a corresponding joint axis and having a plurality of artificial muscles comprising smart materials affixed thereto wherein said artificial muscles are in signal communication with a system of sensors mounted on said member, said sensors detecting environmental stimulation of said member and producing detection signals corresponding to said stimulation, said sensors farther transmitting said detection signals to command circuitry in electrical communication with said artificial muscles so as to effect anthropometrical movement of said member in response thereto, said artificial muscles being arranged electrically in a combination of series and parallel current paths such that upon application of voltage to said artificial muscles a change in dimension of said artificial muscles is effected, to thereby cause movement of said member.

55. The device of claim 54, wherein said artificial muscles are mechanically connected between a pair of end plates.

56. The device of claim 54, wherein said artificial muscles are fixed proximate said joint axis to enable large angular movements of said articulated member.

57. The device of claim 54, wherein at least one of said artificial muscles is folded in an overlapping configuration along a length of said articulated member.

58. An assistive device actuated by artificial muscles which provides increased dexterity and agility of an artificial or dysfunctional limb, comprising:

an articulated member having at least one joint pivotable about a corresponding joint axis and having a plurality of artificial muscles comprising smart materials affixed thereto wherein said artificial muscles are in signal communication with a system of sensors mounted on said member, said sensors detecting environmental stimulation of said member and producing detection signals to command circuitry in electrical communication with said artificial muscles so as to effect anthropometrical movement of said member in response thereto, said artificial muscles comprising a bundle of elongate elements that are adapted to change dimension in response to said detection signals resulting in expansion or contraction of such elements and movement of said member.

59. An assistive device according to claim 58, wherein said detection signals are adapted to provide a voltage to said elements.

60. An assistive device according to claim 58, wherein said detection signals are adapted to provide pressure to said elements.

61. An assistive device according to claim 58, wherein said detection signals are adapted to provide a change in temperature to said elements.

62. A method of effecting movement of an artificial limb comprising of steps of:

providing an artificial limb having an articulated support member releasably mounted to a patient;

attaching a plurality of artificial muscles comprising smart materials to said articulated support member for movement of said member corresponding to contraction or expansion of said artificial muscles; and subjecting selected artificial muscles to a physical condition to cause a change in dimension of said selected artificial muscles, resulting in contraction or expansion of such artificial muscles and thereby effecting movement of said articulated member.

63. The method of claim 62, wherein said subjecting step comprises the application of voltage to said selected artificial muscles.

64. The method of claim 62, wherein said subjecting step comprises the application of pressure to said selected artificial muscles.

65. The method of claim 62, wherein said subject step comprises the application of a change in temperature to said selected artificial muscles.

66. The method of claim 62, wherein said artificial muscles are provided in communication with residual muscles of said patient for communicating electromyographic signals to said artificial muscles so as to produce said physical condition.

* * * * *